United States Patent
James et al.

(10) Patent No.: US 12,136,217 B2
(45) Date of Patent: Nov. 5, 2024

(54) MAGNETIC-RESONANCE-BASED METHOD FOR MEASURING MICROSCOPIC HISTOLOGIC SOFT TISSUE TEXTURES

(71) Applicant: BIOPROTONICS, INC., Santa Barbara, CA (US)

(72) Inventors: Timothy W. James, Santa Barbara, CA (US); Kristin James, Santa Barbara, CA (US)

(73) Assignee: BIOPROTONICS, INC., Santa Barbara, CA (US)

( * ) Notice: Subject to any disclaimer, the term of this patent is extended or adjusted under 35 U.S.C. 154(b) by 369 days.

(21) Appl. No.: 17/577,098

(22) Filed: Jan. 17, 2022

(65) Prior Publication Data
US 2022/0230315 A1    Jul. 21, 2022

Related U.S. Application Data

(60) Provisional application No. 63/138,660, filed on Jan. 18, 2021.

(51) Int. Cl.
| | |
|---|---|
| *G06T 7/00* | (2017.01) |
| *A61B 5/00* | (2006.01) |
| *A61B 5/055* | (2006.01) |
| *G01R 33/54* | (2006.01) |
| *G01R 33/56* | (2006.01) |

(52) U.S. Cl.
CPC ............ *G06T 7/0014* (2013.01); *A61B 5/055* (2013.01); *A61B 5/7257* (2013.01); *G01R 33/543* (2013.01); *G01R 33/5608* (2013.01); *G06T 2207/10088* (2013.01); *G06T 2207/30081* (2013.01)

(58) Field of Classification Search
CPC ......... G06T 7/0014; G06T 2207/10088; G06T 2207/30081; G01R 33/543
See application file for complete search history.

(56) References Cited

FOREIGN PATENT DOCUMENTS

WO    WO2019010381    * 10/2019    ............ G01R 33/46

* cited by examiner

*Primary Examiner* — Myron Wyche
(74) *Attorney, Agent, or Firm* — Felix L. Fischer

(57) ABSTRACT

A method for measuring soft tissue texture to identify diseased as opposed to normal tissue by identifying textural markers that distinguish diseased tissue from normal tissue and selecting a MRµT excitation sequence and associated parameters to reveal those markers. Data is then acquired in an MR scanner responsive to the selected MRµT excitation sequence to establish a multipoint time series data set. The acquired data is then analyzed for presence of the markers.

9 Claims, 14 Drawing Sheets

HISTOLOGY SHOWING ANALYSIS REGIONS

HIGH RESOLUTION PRE-CLINICAL MRI OF MATCHING TISSUE SPECIMEN

MAGNETIC-RESONANCE-BASED METHOD FOR MEASURING MICROSCOPIC HISTOLOGIC SOFT TISSUE TEXTURES

REFERENCES TO RELATED APPLICATIONS

This application claims priority of U.S. provisional application Ser. No. 63/138,660 filed on Jan. 18, 2021 entitled MAGNETIC-RESONANCE-BASED METHOD FOR MEASURING MICROSCOPIC HISTOLOGIC SOFT TISSUE TEXTURES, having a common assignee with the present application, the disclosure of which is incorporated herein by reference

BACKGROUND

Field

The disclosure herein relates to the field of diagnostic assessment of fine textures in biological systems for pathology assessment and disease diagnosis. More specifically, the implementations disclosed herein provide methods for repeat measurement of signal at k-values associated with the spatial organization of biologic tissue texture, with excitation employed in an MR scanner in one of (A) a Continuous Scan method, employing a continuous encode implementation of a magnetic resonance micro texture (MRµT) pulse sequence. (B) An implementation of a Targeted and Discrete Set MRµT pulse sequence capturing a discrete set of k-encoded signals from an excitation, or (C) Multiple TR scans with each TR generating a single spin echo with a single k-encode to generate a set of measurements (spectrum) of texture for the VOI being analyzed. Textural markers that distinguish diseased tissue from normal (raises question re fibrotic disease) are identified and the MRµT method and acquisition/analysis parameters to reveal said markers are selected. Data is then acquired in an MR Scanner and analyzed for presence of the markers

Related Art

The use of Magnetic Resonance (MR) imaging in disease diagnosis is rapidly increasing across a broad range of pathologies—it is a powerful and rich technology with many opportunities for technique improvement.(see V. Kasivisvanathan and et al., "MRI-Targeted or Standard Biopsy for Prostate-Cancer Diagnosis.," *The New England journal of medicine*, vol. 378, no. 19, pp. 1767-1777, 2018 and C. E. Comstock and et al., "Comparison of Abbreviated Breast MRI vs Digital Breast Tomosynthesis for Breast Cancer Detection Among Women With Dense Breasts Undergoing Screening.," *JAMA*, vol. 323, no. 8, pp. 746-756, 2020). Obtaining texture information, defined herein as Magnetic Resonance micro-texture (MRµT), MRµT technology or the as the MRµT method, is disclosed in U.S. Pat. No. 9,366,738, and associated U.S. Pat. Nos. 9,664,759, 9,664,760, 10,061,003, 10,215,827, 10,330,763, 10,955,503 and 11,175,363 (the disclosures of which are incorporated herein by reference) provides direct methods for evaluating pathologic tissue structure to the tens of microns resolution level—greatly increasing the resolution of MR for measuring tissue micro morphology and establishing methods wherein MRµT has the potential to be used as a non-invasive replacement for biopsy.

A non-invasive histology diagnostic with this resolution can provide highly desired information that is not available with current diagnostic MR imaging. U.S. Pat. No. 9,366,738 describes the method whereby this resolution is achieved in an MR scanner by focusing on acquisition of only the quantitative microscopic texture data needed for disease assessment rather than on gathering the entire set of data required to generate an image.

| Table of terms: | |
|---|---|
| MR | Magnetic Resonance |
| VOI | Volume of Interest/sampling volume |
| k-space. | is an array of numbers representing spatial frequencies in the MR image |
| k-value | One spatial frequency |
| MRµTexture | Magnetic Resonance Micro-texture |
| MRµT | Magnetic Resonance Micro-texture |
| In silico | performed on a computer or via computer simulation |
| Chemical shift | is the resonant frequency of a nucleus relative to a standard (e.g., water) in a magnetic field |
| Phase cycling | Suppression of unwanted MR signals by changing the receiver phase and pulsed excitation phase with respect to the reference signal and spin magnetization phase |
| Signal echo | The refocused signal obtained by flipping the orientation of the spins such that they regain phase |
| Tissue texture | Microstructural patterns within tissue |
| TR | Repetition Time is the time between 2 excitations pulses (time between two 90° RF pulses) |
| SNR | Signal to Noise Ratio |
| CNR | Contrast to Noise Ratio-the contrast obtained in a measurement between the various textural features that enables clearly distinguishing them to highlight the micro-morphology of the tissue texture |

SUMMARY

A method is disclosed for obtaining soft tissue texture to identify diseased as opposed to normal tissue by identifying textural markers that distinguish diseased tissue from normal tissue and selecting a MRµT excitation sequence and associated parameters to reveal those markers. Data is then acquired in an MR scanner responsive to the selected MRµT excitation sequence to establish a multipoint time series data set. The acquired data is then analyzed for presence of the markers.

BRIEF DESCRIPTION OF THE DRAWINGS

FIG. 1A shows a Continuous Scan method, employing a continuous encode implementation of the MRµT pulse sequence. FIG. 1B shows an implementation of a Targeted and Discrete Set MRµT pulse sequence capturing a discrete set of k-encoded signals from an excitation. FIG. 1C shows a Multiple TR implementation incorporating a multi-TR sequence with each TR generating a single spin echo with a single k-encode to generate a set of measurements (spectrum) of texture for the VOI being analyzed.

FIGS. 2A and 2B demonstrate an idealized hydrogel specimen for resolution validation, wherein FIG. 2A is an optical micrograph of a 3D-printed honeycomb nanostructure looking down the channels, which have a measured interplanar spacing of ~39 μm as indicated by the distance between the overlaid bars and FIG. 2B is a graph of 62 MRμT measurements acquired using the Multiple TR sequence of signal strength vs. textural wavelength between 30 μm and 45 μm exhibiting a peak at ~39 μm as expected and as indicated by the distance between the overlaid bars in FIG. 1A. The FFT of the acquired spin echoes show chemical-shift peaks at 0.2 and 0.3 ppm corresponding to the hydrogel and saline medium, respectively; the data in FIG. 2B plots the integrated area under the hydrogel peak for each k-encoded measurement. It should be noted that due to the high structural coherence of this sample, careful alignment of the analysis direction to the array was required.

FIGS. 4A and 4B demonstrate a spectrum illustrating the ability to characterize textures in biologic specimens, wherein FIG. 4A is a plot of measurements from a pig liver specimen using the Multiple TR MRμT method. The VOI size i 4×4×8 mm and TR was 2000 msec and FIG. 4B is an MSME image of the liver showing the hepatic lobules, collagen walls and central veins in the region of the specimen analyzed.

DETAILED DESCRIPTION

Figure 1A:
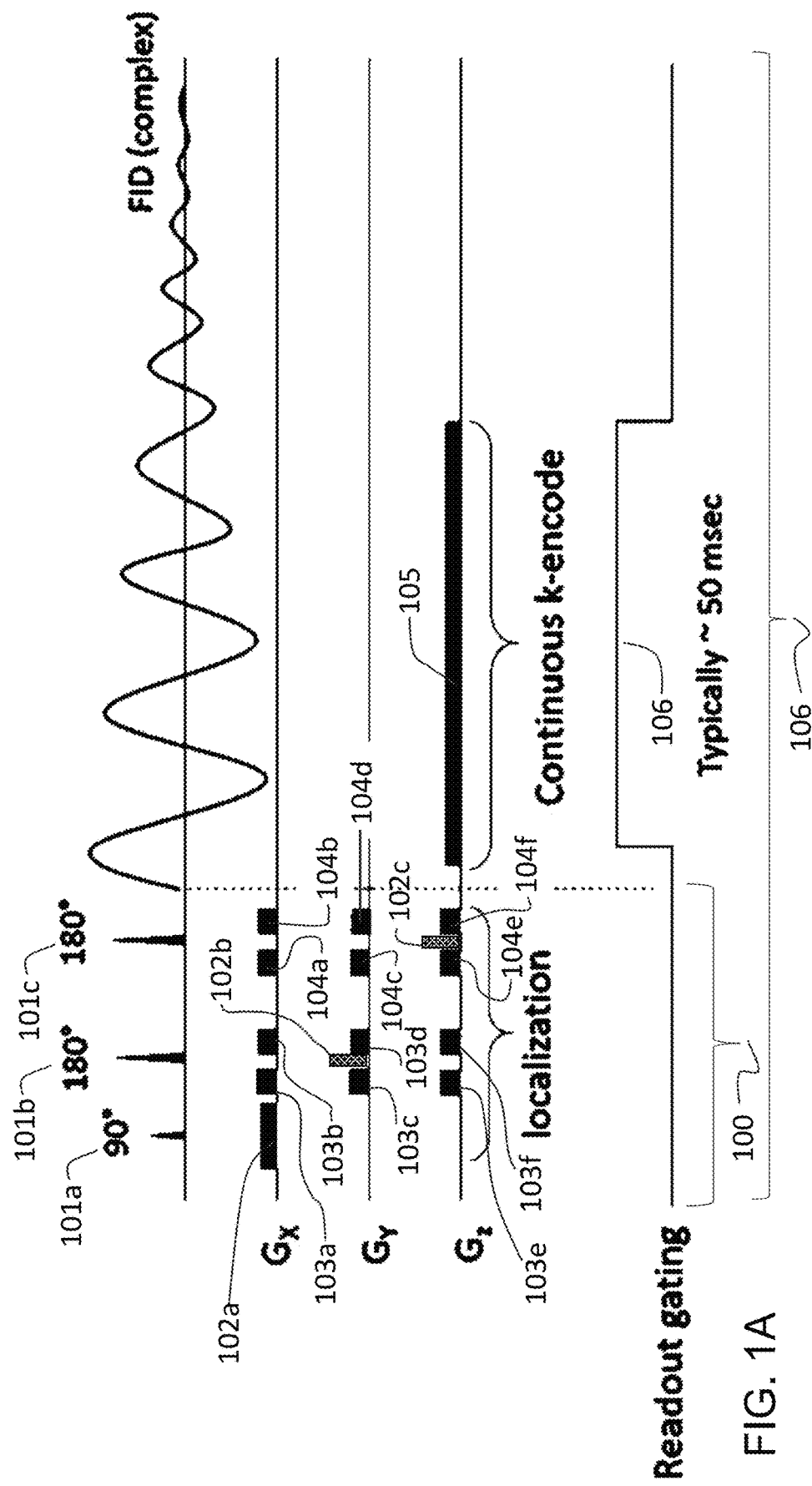
FIGS. 1A, 1B and 1C graphically demonstrate three excitation methods wherein the rectangles represent slice-select gradients, crusher gradients, or k-encoding gradients. The z-axis (Gz) is the texture analysis direction, the direction upon which the k-encodes are impressed. All three utilize a PRESS sequence to generate a selective internal excitation of a VOI. Other sequences including the STEAM sequence can be used to generate an internal selective excitation.

MR micro-texture (MRμT), is a direct method for evaluating pathologic tissue structure to the tens of microns resolution level. A non-invasive histology diagnostic with this resolution would provide highly desired information that is not available with current diagnostic imaging. This resolution is achieved by focusing on acquisition of only the quantitative microscopic texture data needed for disease assessment rather than on gathering the entire set of data required to generate an image. As an example of the many biologic tissue systems that would benefit from quantitative histology measurements, made non-invasively by MR, MRμT data was acquired from radical prostatectomy tissue with corresponding whole organ optical histology for ground truth. The MRμT data reveal significant differences in tissue texture between cancerous and normal prostate tissue. Current clinical practice relies on indirect MR measures (e.g. DWI, elastography, T2 . . . ) and biopsy towards disease diagnosis, the micro-textural tissue feature morphology being not resolvable by current imaging techniques. The MRμT technology, which has the potential to replace biopsy, is implemented as a new MR pulse sequence. As this is done in software without any requirements for new hardware, it is directly translatable to MRI scanners currently in clinical practice, enabling broad adoption to meet the urgent need for improvement in cancer imaging (see Y. X. Kitzing, A. Prando, C. Varol, G. S. Karczmar, F. Maclean and A. Oto, "Benign Conditions That Mimic Prostate Carcinoma: MR Imaging Features with Histopathologic Correlation.," *Radiographics*, vol. 36, no. 1, pp. 162-175, 2016).

In order to maximize the accuracy of diagnosis in specific soft tissue diseases, optimization of data acquisition and analysis parameters for application of the MRμT method to the targeted disease is required. Biologic tissue phantoms were used to verify the ability for sub-100 μm resolution provided by this paradigm-changing method when applying it to prostate disease diagnosis and staging. The changes in tissue microstructure accompanying development of prostate disease is one example of the many biologic tissue systems that would hugely benefit from high resolution quantitative histology measurements made non-invasively by MR. Towards diagnosis and staging of prostate disease specific acquisition and analysis methods/parameters are defined herein for application of the MRμT method for acquisition and analysis of the MRμT data as a diagnostic for this disease.

Prostate cancer is the second leading cause of death for men in the US, behind only lung cancer. One man in 41 will die of prostate cancer. (www.cancer.org American cancer society.) However, the issue of prostate cancer screening is controversial—disease diagnosis is fraught due to the multiple presentations of the disease which often results in over diagnosis and over treatment.

The disclosure herein provides enhanced diagnostic capability when employing the MRµT diagnostic method. This capability enables application of the MRµT technology methods disclosed in that patent to diagnosis and staging of prostate disease and other soft tissue diseases and pathology,) (including the various pathologic presentations associated with COVID-19.) The details of these methods, introduced herein, define optimal methods of application of MRµT in diagnosis and staging of a range of soft tissue diseases and pathologies, focusing on its application to prostate disease diagnosis and staging.

Optimization of MRµT for Diagnosis and Tracking of Prostate Disease and Other Soft Tissue Diseases Requires Optimizing Data Acquisition and Analysis Methods.

A method to identify diseased vs normal tissue towards grading pathology includes a. Calibrate the MRµT technique for application to prostate disease or other tissue-mediated disease pathology—i.e. develop a transfer function between the morphology of the targeted tissue regions and the MRµT data output from these same tissue regions. This calibration involves performing a sufficient number of correlations between MRµT measure of tissue pathology and biopsy driven histomorphometric measure of tissue pathology, from the same tissue regions, to allow accurate and sensitive determination of the data transfer function. This calibration effort can further rely on in silico calibration—performing in silico MRµT data acquisition from histomorphometric or microCT data sets and using the correlation between these sources of data for calibration development.

b. Identify the textural biomarkers that distinguish diseased tissue from normal. In prostate disease, higher intensity of long textural wavelengths relative to short is an indication of normal tissue, while the opposite—higher intensity of short tissue texture wavelengths relative to long indicates disease onset and progression and can be used to grade disease.

c. Select appropriate parameters for application of MRµT to tissue characterization for the targeted disease to measure the relative variation of signal intensity of the various textural wavelengths. This includes Volume of Interest (VOI) dimensions and orientation, chemical shift ranges for inclusion in the data analysis (as described in U.S. Pat. No. 10,215,827) and extent of the tissue region defined by the VOI length determined as called out in the BW (Bandwidth) method patent (U.S. Pat. No. 10,955,503).

d. Use machine learning and deep learning AI methods, combined with pattern recognition and supervised learning to determine biomarkers from multiple data sets.

e. Analyze the data for presence of these identified markers.

f. Identification of the difference in tissue texture arising from changes in vasculature in health vs. in tumor-containing prostate tissue.

In contrast to current clinical imaging, MRµT data acquisition is immune to subject motion by virtue of using a single excitation for each spatial wavelength measurement that contributes to the data set characterizing the tissue texture. This enables high-resolution, non-invasive measurement of textures in the important sub-100 µm range. This motion immunity is key to avoiding the limitations of traditional clinical MR imaging in which unintentional and involuntary patient movements limit resolution. (see I. Haysteen, A. Ohlhues, K. H. Madsen, J. D. Nybing, H. Christensen and A. Christensen, "Are Movement Artifacts in Magnetic Resonance Imaging a Real Problem?-A Narrative Review.," *Front Neurol.*, vol. 8, p. 232, 2017). The high-resolution provided by MRµT has the potential to not only identify cancerous lesions, by changes in tissue morphology in the region of these lesions, but also to specifically identify cancer grade, while reducing the need for biopsy.

Disclosed herein as a specific example are methods for optimization of the MRµT data acquisition and data analysis and for applying these to diagnosis and staging of prostate, combining them with the current standard of care, such as the mpMRI pulse sequences used in prostate lesion identification and grading.

Parameter optimization for application of MRµT in prostate disease diagnosis was accomplished through use of fixed tissue wholemount blocks cut from radical prostatectomy tissue. MRµT data acquisition from these radical prostatectomy tissue blocks, correlated with corresponding whole organ histomorphometry from adjoining tissue for ground truth, enables accurate calibration of the MRµT technique for application in prostate tissue characterization towards diagnosis and staging. The MRµT data exhibit significant differences in tissue texture between cancerous and normal prostate tissue. The direct measure of tissue morphology provided by MRµT enables a more sensitive/accurate measure of tissue microstructure than is possible with the indirect DWI measure performed as part of the current mpMRI evaluation. DWI is an inferential measure, which means that the acquired data can reflect a range of underlying tissue microstructures making exact correlation with tissue pathology difficult.

The current clinical standard of care is moving in the direction of use of MR imaging with added DWI/ADC and T2 signal decay changes—i.e. mpMRI tissue characterization and tumor localization. mpMRI increases the accurate localization of prostate cancer at the time of MRI targeted biopsy thereby enhancing clinical risk assessment. Though standard MR imaging can highlight lesions in the tissue, due to patient motion the resolution available is insufficient to provide high sensitivity morphology characterization of pathologic tissue and tumor localization. Hence, the addition of the DWI sequences to generate the mpMRI metric. Though DWI is able to probe tissue texture at the cellular level, as outlined above inferential measures such as DWI are unable to provide the high resolution required for highly accurate biopsy guiding. Biopsy driven histomorphometry provides the highest resolution measure available of tissue morphology to track pathology but suffers from sampling errors and is highly invasive with not-insignificant associated morbidity.

Multiparametric-MRI (mpMRI) is an evolving noninvasive imaging modality that increases the accuracy of localization of prostate tumors for targeted biopsy, thereby enhancing clinical risk assessment, and improving the ability to appropriately counsel patients regarding therapy. However, this modality is challenged by the inferential nature of DWI. By contrast, MRµT is a direct measure of tissue morphology and, as such, is able to directly measure the tissue changes in the vicinity of tumors that highlight tissue pathology, enabling clear localization.

The MRµT technology, which has the potential to replace biopsy in prostate diagnosis, is implemented as a new MR pulse sequence. As this is done in software without any requirements for new hardware, it is directly translatable to MRI scanners currently in clinical practice, enabling broad adoption to meet the urgent need for improvement in cancer imaging.(see Y. X. Kitzing, A. Prando, C. Varol, G. S. Karczmar, F. Maclean and A. Oto, "Benign Conditions That Mimic Prostate Carcinoma: MR Imaging Features with Histopathologic Correlation.," *Radiographics*, vol. 36, no. 1, pp. 162-175, 2016). This opens the ability to apply MRµT measurement of prostate pathology in parallel with DWI.

The disclosure herein provides enhancements to the MRµT methods, to facilitate application of the novel tissue texture diagnostic disclosed therein to prostate disease and other soft tissue disease diagnosis. These enhancements include methods of generating contrast to acquire MRµT data, as well as to analyze the data from MRµT measurements of prostate, and other soft tissue disease pathology, for diagnosis, staging, and monitoring, of disease, as well as for application to other tissue pathologies.

Additionally, disclosed are certain benefits and methods for combining MRµT data acquisition with data acquisition methods similar to ASL (Arterial Spin Labeling) and DWI (Diffusion Weighted Imaging). In contrast to current clinical imaging, MRµT data acquisition is immune to subject motion by virtue of using a single excitation for each k-value (or spatial wavelength) measurement that contributes to the data set characterizing the tissue texture. This enables high-resolution, non-invasive measurement of textures in the important sub-100 µm range. This motion immunity is key to avoiding the limitations of traditional clinical MR imaging in which unintentional and involuntary patient movements including respiration, cardiac pulsation, bowel peristalsis, and bladder motion limit resolution.(see I. Haysteen, A. Ohlhues, K. H. Madsen, J. D. Nybing, H. Christensen and A. Christensen, "Are Movement Artifacts in Magnetic Resonance Imaging a Real Problem?-A Narrative Review.," *Front Neurol.*, vol. 8, p. 232, 2017). The high-resolution provided by MRµT has the potential to not only identify cancerous lesions, but also to specifically identify aggressive cancers by resolving different cancer grades, while potentially avoiding the need for biopsy. Along with being a good model for many soft tissue diseases, prostate cancer was chosen as a first demonstration of clinical potential because of the availability of tissue specimens with corresponding whole-organ histology, which provides one-to-one spatial correspondence of the MRµT measures with high resolution ground truth histology, and because of the significant unmet clinical need for improved prostate cancer diagnosis. An additional motivation for this focus is that the utilization of MR imaging in prostate cancer diagnosis and treatment is rapidly increasing.(see A. Stabile and et al., "Multiparametric MRI for prostate cancer diagnosis: current status and future directions.," *Nature reviews. Urology*, vol. 17, no. 1, pp. 41-61, 2020; S. Sarkar and S. Das, "A Review of Imaging Methods for Prostate Cancer Detection.," *Biomedical engineering and computational biology*, vol. 7, no. Suppl 1, pp. 1-15, 2016 and M. Ahdoot and et al., "MRI-Targeted, Systematic, and Combined Biopsy for Prostate Cancer Diagnosis.," *The New England journal of medicine*, vol. 382, no. 10, pp. 917-928, 2020) Recent studies demonstrate the value of current MRI protocols in tandem with elevated serum prostate specific antigen (PSA) levels for selecting patients for biopsy and in guiding biopsy to improve cancer diagnosis.(see O. Rouvière and et al., "Use of prostate systematic and targeted biopsy on the basis of multiparametric MRI in biopsy-naive patients (MRI-FIRST): a prospective, multicentre, paired diagnostic study.," *The Lancet. Oncology*, vol. 20, no. 1, pp. 100-109, 2019; V. Kasivisvanathan and et al., "MRI-Targeted or Standard Biopsy for Prostate-Cancer Diagnosis.," *The New England journal of medicine*, vol. 378, no. 19, pp. 1767-1777, 2018; and D. Lomas and H. Ahmed, "All change in the prostate cancer diagnostic pathway.," *Nat Rev Clin Oncol.*, vol. 17, no. 6, pp. 372-381, 2020.) Yet, unmet challenges remain including more accurate prostate cancer detection on MRI, reducing inter-reader variability, non-invasive differentiation of indolent vs. aggressive prostate cancer, reducing long acquisition times, and reducing susceptibility to motion artifact. (see A. Westphalen and et al., "Variability of the Positive Predictive Value of PI-RADS for Prostate MRI across 26 Centers: Experience of the Society of Abdominal Radiology Prostate Cancer Disease-focused Panel.," *Radiology*, vol. 296, no. 1, pp. 76-84, 2020). Because MR imaging is widely available, improvements in diagnostic capabilities, particularly ones that can be implemented in software, have the potential to make a major impact in cancer care.

Disease happens quietly. Changes begin at the very smallest levels of the anatomy, affecting the microscopic structure of the biologic tissue of which organs are composed. A huge unmet need in healthcare is the ability to assess these very fine changes, before they lead to irreversible pathology accumulation. The list of diseases for which accurate measure of microscopic tissue changes would enable sensitive diagnosis is extensive. It includes bone disease, bone degradation from cancer treatment, diseases marked by fibrotic development, such as liver disease, lung disease, kidney disease, and cardiac disease, neurologic diseases and conditions including the various forms of dementia, multiple sclerosis, cerebrovascular disease, and tumor formation in a range of cancers. Hence, MRµT provides a powerful tool to apply to the task of unraveling disease pathophysiology, enabling diagnosing and monitoring progression in a disease. For a disease such as COVID-19, a hallmark of which is its multi-organ attack with hugely varied presentation and course, this ability to measure pathology in many, highly varied organ tissues, enables a direct correlation of pathology across organs and across the anatomy.

Currently, the only direct way to measure microscopic changes in biologic tissue texture is biopsy, an invasive procedure, fraught with sampling errors—biopsies often miss their intended target—such as a small tumor that the needle slips by. Further, the invasiveness of biopsy limits its use to specific organs, and ability to repeat studies for longitudinal tracking of disease and therapy response is limited. Also, application of biopsy to an immune-compromised patient is contra-indicated.

Though MR imaging is the diagnostic of choice in a wide range of diseases due to its ability to non-invasively provide tunable tissue contrast to highlight variations in the anatomy, spatial resolution in MR imaging is limited by blurring caused by patient motion. This makes it impossible to image the microscopic changes in tissue texture that signal disease onset, or that are needed to sensitively track disease progress. Even using cardiac and respiratory gating schemes or real-time motion correction, and with a compliant patient, resolution is not high enough to measure microscopic tissue texture. Certain MR contrast mechanisms such as DWI (Diffusion-Weighted-Imaging) look at signals affected by the microscopic texture of biologic tissue, however the signals obtained by use of this method are indirect, and hence not unique—multiple different underlying cellular states can be responsible for a specific output signal measurement—there is not a one-to-one correspondence.

As a result of this inability to measure biologic tissue texture at high resolution, noninvasively (in vivo), much nascent pathology goes undetected because the microscopic biologic tissue changes attendant with disease onset and progression are outside the resolution capability of current clinical imaging techniques. Not only does this affect outcomes, but the inability to target subject participants early enough in disease course seriously hampers therapy development efforts. Additionally, there is no means to determine and track disease pathophysiology with high resolution as is needed for therapy development efforts. It is this challenge—obtaining in vivo, noninvasive, clinically robust, high resolution MR measure of tissue texture—that the MRµT technology was designed to solve.

The MRµT technology uses the fact that magnetic resonance scanners acquire data in diffraction space (k-space), to allow design of an MR data acquisition sequence that enables motion immune, hence very high resolution, acquisition of tissue texture measurement data. Diffraction space is comprised of a matrix of signal at each of the spatial frequencies that contribute to an image—this spectrum being obtained by Fourier analysis. To generate a high-resolution image, a very large data set is required starting at k=0 and continuing up to the highest frequency Fourier component present in the image. This can be understood with reference to a spectrum analyzer such as the sound analyzers once built into some stereo systems. An audio spectrum analyzer breaks down an acoustic waveform as a spectrum of its component audio frequencies, outputting a spectrum of signal strength vs. intensity of each of the sound frequencies that contribute to the audio signal. Diffraction space is simply a plot of MR image data that shows the relative contribution (intensity) of each spatial frequency that comprises an MR image. Applying a Fourier transform to this frequency-space data yields the MR image. But, to form an image, the relative intensity of a continuous range of spatial frequencies must be measured in the anatomy to be imaged with the same phase reference, from 0 (the DC-value) up through the highest spatial frequency desired. The smaller the feature in the anatomy, the greater the range of spatial frequencies that must be recorded to resolve it in the image. The problem is that the large range of spatial frequencies needed to form an image makes for a very large data set, especially as spatially resolved data must be acquired across the entire organ being imaged. As a result, the SNR (Signal to Noise Ratio) for each individual data point in the acquisition is low. This problem of low SNR is exacerbated by the fact that signal amplitude varies inversely with spatial frequency—higher resolution features generally have lower signals. Therefore, multiple excitations are required for signal averaging to boost SNR. But over the time needed to acquire all this data patients are moving, and the image is blurring, so that very fine features will not be resolvable. In MR imaging, the need to acquire data across a large range of spatial frequencies in each excitation, and across a large spatial extent, results in motion-limited tissue texture resolution.

By contrast, MRµT enables a very high-resolution, clinically robust measure of tissue texture by focusing on measuring the signal intensity of only those spatial frequencies pertinent to the targeted pathology, and not trying to build up an image. Motion from one excitation to the next does not affect this measurement. The only requirement on patient motion using MRµT is that the sampling volume remain within a similar region of tissue during the time the various spatial frequency intensities are measured to characterize the tissue—a much more lenient requirement than the spatial phase coherence that is needed for imaging. The MRµT diagnostic provides a new quantitative MR measure that enables in vivo tissue texture measure anywhere in the anatomy, allowing mapping of tissue texture state across organs, with the ability to repeat the measure as often as a patient is in the scanner, to determine and track pathophysiology.

The enhancements disclosed herein include methods of generating contrast and analyzing data for soft tissue pathologies and, as a specific example herein, prostate disease diagnosis, staging, and monitoring. A method and data demonstrating the ability to measure these microscopic pathologic tissue textures (histology) in the presence of subject motion in an MR scanner. This size range is vital to diagnosing a wide range of diseases.

Magnetic Resonance micro-Texture (MRµT) resolves these textures by a combination of measuring a targeted set of k-values to characterize texture—as in diffraction analysis of materials, performing a selective internal excitation to isolate a VOI, applying a high k-value phase encode to the excited spins in the VOL and acquiring each individual k-value data point in a single excitation—providing motion immunity and extended acquisition time for maximizing SNR. Additional k-value measurements from the same tissue can be made to characterize the tissue texture in the VOI—there is no need for these additional measurements to be spatially coherent as there is no image to be reconstructed. This method was applied to phantoms and tissue specimens including human prostate tissue.

Radiomics, a form of MR image post-processing that highlights textures in the image, has been previously reported.(see B. Varghese and et al., "Objective risk stratification of prostate cancer using machine learning and radiomics applied to multiparametric magnetic resonance images.," *Scientific reports*, vol. 9, no. 1, p. 1570, 2019; C. Nguyen and et al., "Novel magnetic resonance technique for characterizing mesoscale structure of trabecular bone.," *Royal Society open science*, vol. 5, no. 8, p. 180563, 2018; H. J. Meyer, S. Schob, A. K. Höhn and A. Surov, "MRI Texture Analysis Reflects Histopathology Parameters in Thyroid Cancer—A First Preliminary Study.," *Translational oncology*, vol. 10, no. 6, pp. 911-916, 2017; A. Kassner and R. E. Thornhill, "Texture analysis: a review of neurologic MR imaging applications.," *AJNR. American journal of neuroradiology*, vol. 31, no. 5, pp. 809-816, 2010; and Y. Zhang, C. Chen, Z. Tian, R. Feng, Y. Cheng and J. Xu, "The Diagnostic Value of MRI-Based Texture Analysis in Discrimination of Tumors Located in Posterior Fossa: A Preliminary Study," *Frontiers in neuroscience*, vol. 13, p. 1113, 2019). However, no degree of image analysis will produce textural detail at resolution finer than what was initially acquired—higher resolution raw data is required to increase measurement resolution. Currently, resolution achievable in a clinical setting by MRI or CT is limited by blurring resulting from unavoidable involuntary patient motion during the multiple excitations required for to generate an image. (see E. Lin and A. Alessio, "What are the basic concepts of temporal, contrast, and spatial resolution in cardiac CT?," *Journal of cardiovascular computed tomography*, vol. 3, no. 6, pp. 403-408, 2009)and is generally insufficient to measure the histologic texture differences between normal and diseased tissue. The addition of microscopic quantitative histology measures to radiomics and texture analysis would be expected to significantly enhance the sensitivity and specificity of these methods when applied to diagnostic imaging. Tissue/disease cases for which a non-invasive measure of histologic texture would be valuable include organ fibrosis (e.g., liver and cardiac), vascular networks in oncology, and glandular changes as in prostate cancer.

The MRµT method achieves its sensitivity to histologic texture by relying on the combination of four principles: 1) Focusing on texture analysis rather than image generation—i.e. making direct measure of a series of k-values characteristic of the tissue morphology, obtained by measuring the intensity of each phase encoded signal, analogous to diffraction measurements in crystallography. 2) This, in combination with the use of selective internal excitation, provides a means for analysis of texture in a localized VOI. 3) The signals are low for very small textures (<100 µm), hence the use of a single, or small set of, k-encode(s) per excitation provides extended time for recording the spin echo for each individual k-encode, thus maximizing SNR. And finally, 4) Motion immunity—as is known in diffusion measurements, the use of a single excitation enables sensitivity to extremely small dimensions that would be lost in signal averaging methods relying on multiple excitations.

Expanding on point #1 above, two extreme cases illustrate how a phase encode is sensitive to texture: a) for a specimen with uniform and homogeneous tissue, imposition of a phase encode will generate no signal, b) the case of a specimen with repeating patterns with wavelength matching the phase encode will generate a strong signal(see Allen D. Elster, "Signal and Spatial Frequency," 2020. [Online]. Available: https://mriquestions.com/why-signal-harr-k-space.html. [Accessed 20 11 2020). MRµT completes both phase encode and measurement in a single MR excitation, therefore it is inherently immune to motion during signal recording. This immunity arises because the excited and encoded spins move with the tissue regardless of translation, rotation, or distortion of the tissue. Additional textural-wavelengths can be probed in the target tissue by repeating the excitation and encode using varied k-values, thereby building up a sampling of k-space pertinent to the pathogenesis of a disease. As these are independent measures at targeted k-values, there is no requirement for spatial coherence across measurements as there is in image reconstruction.

Motion tolerance stems from two phenomena. The first is that the coil (antenna) receives signal from everywhere within its field. Provided the displacement is not a large fraction of the antenna field, the encoded-tissue-signal phase and magnitude will be minimally altered, i.e., the antenna is largely blind to motion of the encoded signal within the antenna field. Additionally, because the protons in the VOI are independent (no coherence or interference effects), and because the proton spin direction is decoupled from the molecular orientation, once excited and encoded, the excited volume of tissue (VOI) can rotate, distort or change direction of motion during the acquisition period without consequence to the signal. This is true provided, as discussed above, the VOI stays within the receiver and homogeneous B0 volumes.

The second phenomenon guaranteeing motion tolerance is the fact that, though the patient/VOI might move during the application of a field gradient (e.g. during any of the slice-select gradients, the application of any crusher gradients, or the application of any k-encoding gradients), causing protons in the VOI to incur a phase shift, it is straightforward to show that this phase shift will be small for the magnitude and duration of gradients and the range of velocities encountered in a patient. The typical speed of motion for the chest wall during breathing (or tissue motion around a beating heart) is 10-20 mm/s, slow enough that any phase shift is minor and accounted for by recording in quadrature.

Inter-measurement motion tolerance (between consecutive excitations/TRs) is also guaranteed because the signal magnitude at each k-value is acquired independently of the others—it is not necessary to maintain spatial coherence between the measurement of one k-value and the next (or a repeated magnitude measurements); all that is needed is that the VOI remain positioned within a region of similar tissue texture and for anisotropic tissues, e.g., brain cortical neuronal architecture, a similar orientation—a requirement that can be met with automated positioning and respiratory gating.

Rapid tissue motion during the selective VOI excitation will have a minor effect on the fidelity of the boundaries of the VOI. This is likely to be less than that caused by imperfect 180° pulses and does not materially affect the ability to encode and record high-k-encoded measures of texture in the VOI.

MRµT is implemented as a magnetic resonance pulse sequence that: 1) performs a selective internal excitation of a Volume of Interest (VOI) within the targeted tissue region, 2) imposes a spatial- frequency phase encode for the targeted tissue textural-wavelength, λ (or k-value), of interest along the texture analysis direction within the VOI, and 3) records the resulting signal. The key points in this process are, first—utilizing a single excitation to ensure motion immunity, and second—targeting a single (or small set of) encode(s) to obtain a high Signal to Noise Ratio (SNR) measurement within a single excitation. Focusing on a single (or small set of) encode(s) avoids the need for signal averaging by repeated excitations, which in the presence of unavoidable biologic motion limits the obtainable resolution.

The wavelength of the spatial frequency phase encode is calculated as follows:

$$\text{Wavelength(mm)} = 1 / (\text{Phase\_wrap}(1/\text{mm}))$$

$$\text{Phase\_wrap}(1/\text{mm}) = \text{Grad\_cal}\left(\frac{\text{Hz}}{\text{mm}}\right) * \text{Grad\_mag}(\%) / 100 * \text{Grad\_pulse}(s)$$

Where:
Phase_wrap is the number of full 2 π advancements of phase per mm,
Grad_cal is the maximum gradient strength in Hz/mm for 1H,
Grad_mag is the fraction of maximum gradient strength in %,
Grad_pulse is the time duration for the gradient pulse in seconds.
For the prostate tissue analysis reported here, parameter values for a 50 µm wavelength encode were:
Grad_cal=15367 Hz/mm (362 mT/m),
Grad_mag=65.074%,
Grad_pulse=2 ms.

For a high performance 3T clinical scanner with 80 mT/m gradient capability (3400 Hz/mm for 1H) a gradient pulse to encode a wavelength of 50 µm requires Grad_pulse=0.0059 s. Scanners with 40 mT/m gradient capability encoding for 100 µm wavelength features would require the same 5.9 ms gradient pulse. These gradient times are easily incorporated in the pulse sequence—particularly because they are only done once per excitation.

MR Pulse Sequence

There are multiple possible implementations of the MRµT technology of which three were used in this study. In all cases a given texture wavelength is probed by applying a phase encode to a selectively excited internal volume (VOI) defined by a series of intersecting slice selective RF/gradient pulses and recording the resultant spin echo signal. The following is a description of three implementations used to validate the method and to acquire the data from the prostate tissue specimen probed in this study. The choice of excitation method will depend primarily on the available signal level—the Multiple TR method of FIG. 1C by virtue of recording the entire duration of the signal will be best suited to low signal situations (e.g., tissue distant to the receive coils, the smallest textures, and with a low contrast-to-noise between elements of the texture). The Continuous Scan method of FIG. 1A by virtue of only recording a fraction of the signal duration for each increment in k-encode (wavelength) is best suited to cases with ample signal. The Targeted and Discrete Set of FIG. 1B is applicable for intermediate signal situations.

The first variation of an exemplary pulse sequence uses a selective internal excitation and a continuous encode and simultaneous read of a targeted k-value range at a targeted location in the tissue, the "Volume of Interest" or VOI. This "Continuous Scan" method is illustrated in FIG. 1A where an excitation sequence 100 of a series of intersecting slice selective RF/gradient pulses provides the selective internal excitation of the VOI. An RF pulse 101a, slice selection gradients 102a-c, RF refocusing pulse 101b and crusher gradients 103a-103f, second refocusing RF pulse 101c, crusher gradients 104a-104f selectively excite the VOI and establish an initial k-encode. A continuous k-encode 105 is then applied to obtain a selected range of k-values with readout gating 106 during the k-encode pulse. As this is a much smaller set of k values than needed for imaging it enables much higher SNR than available from an image. In the example shown, the z-axis, Gz is the texture analysis direction. An exemplary TR 106 is shown for reference.

Figure 1B:
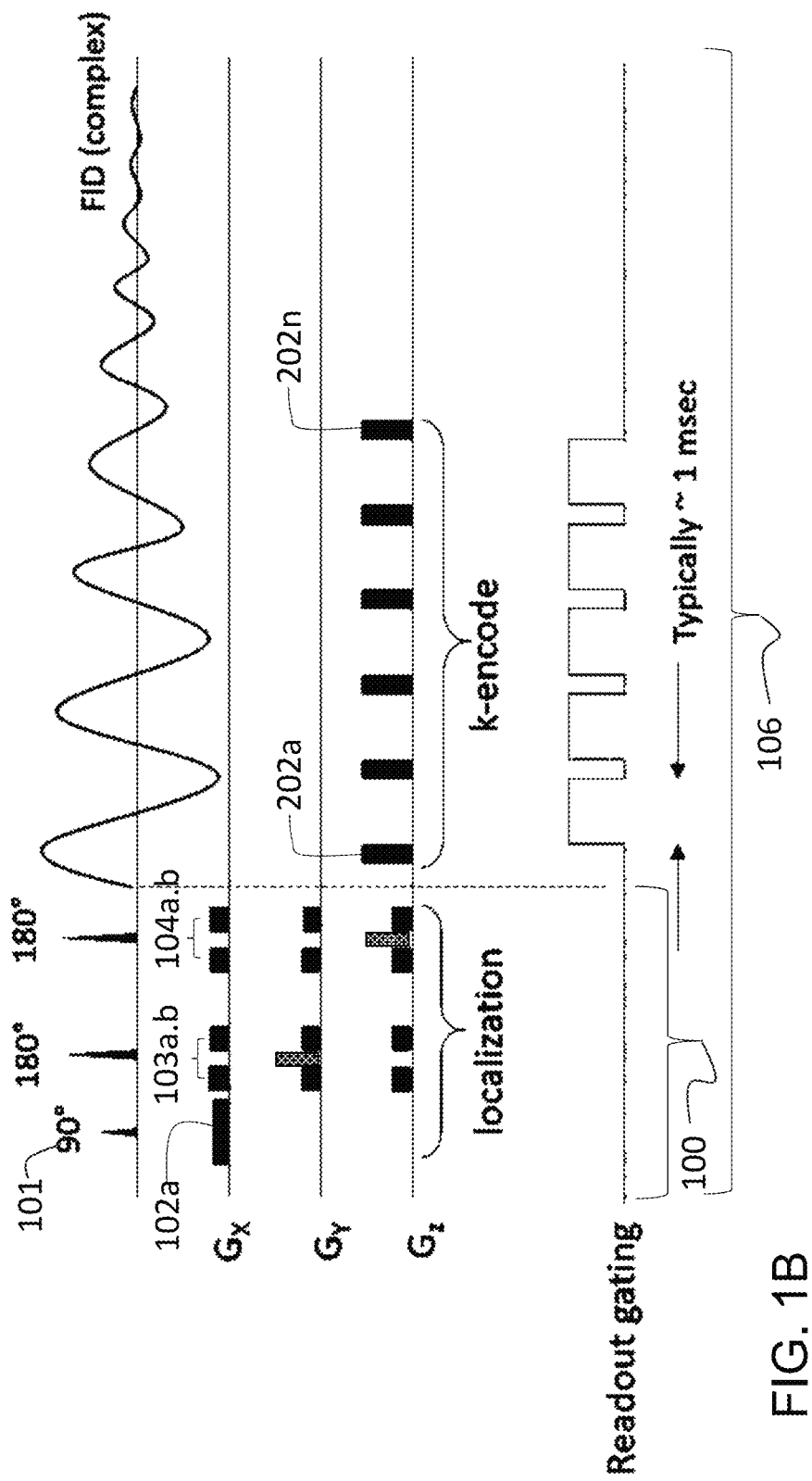

A second variation of the pulse sequence used in the present method uses a targeted, discrete set of k-values encoded into the sample, with incremental phase-encoding and data acquisition occurring after an excitation sequence, a "Targeted and Discrete Set", as shown in FIG. 1B. Following a selective internal volume excitation of the VOI as described above for excitation sequence 100, multiple short k-value encoding gradient pulses 202a-202n, advance the encoding through the targeted set of k-values selected based on anticipated texture induced by the pathology, known from the medical literature and by ground truth histomorphometry studies of disease. Targeting a few select k-values enables acquiring the signal for several milliseconds per k-value, allowing signal averaging to increase the SNR. Readout gating pulses 204a-204n follow each k-value encoding gradient pulse with all gradients off Although not used in these examples, there are additional techniques to increase the SNR including: i) refocusing the echo with multiple 180° refocusing RF pulses, and ii) the combination of data collected from multiple excitations by combining the magnitude of the signals for each excitation, without the need to correct/control for patient motion, as each separate textural wavelength measure is independent-coherence between the measures is not required.

Figure 1C:
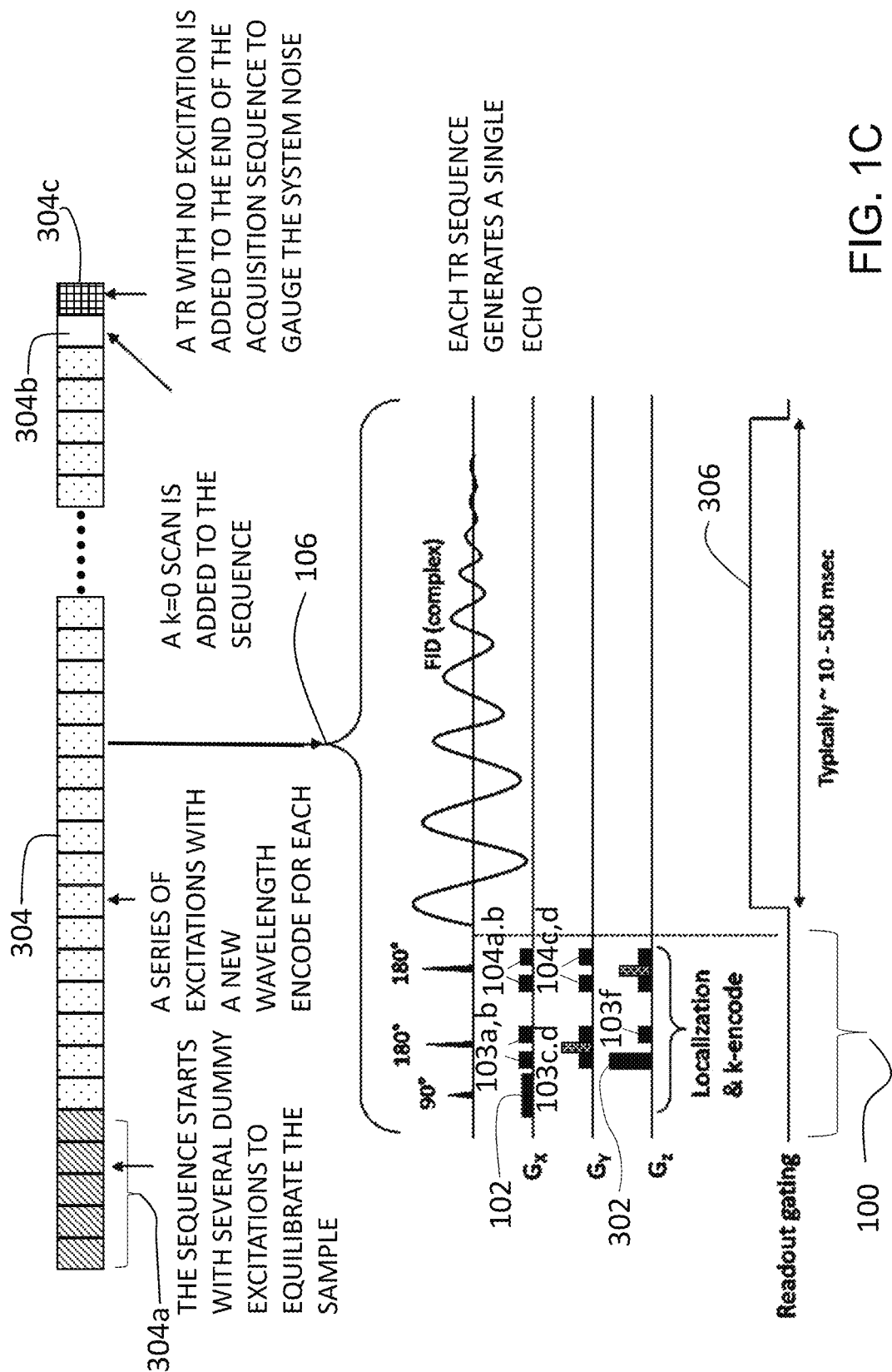
Figure 2A:
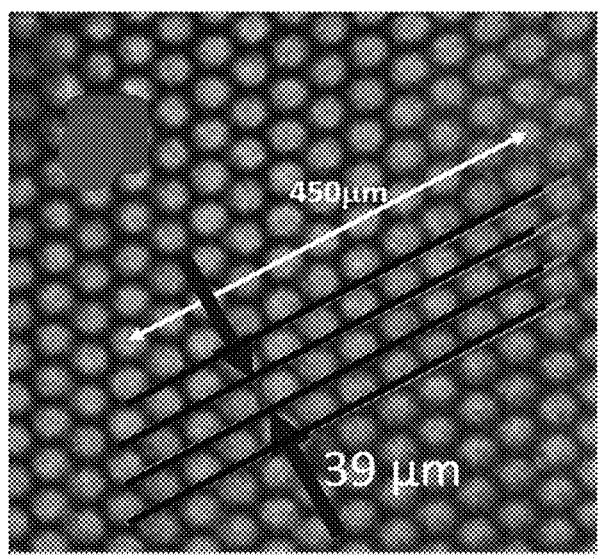
Figure 2B:
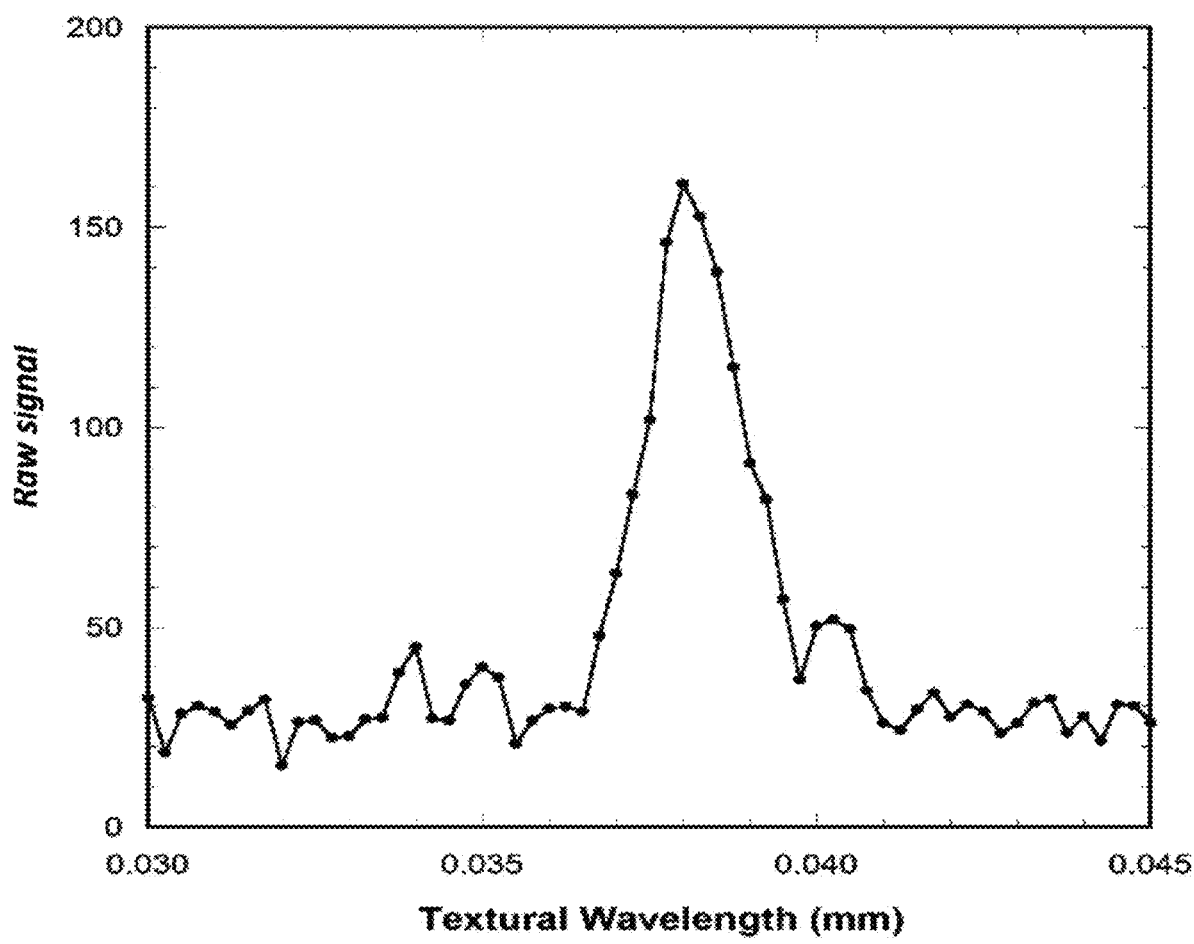
Figure 3:
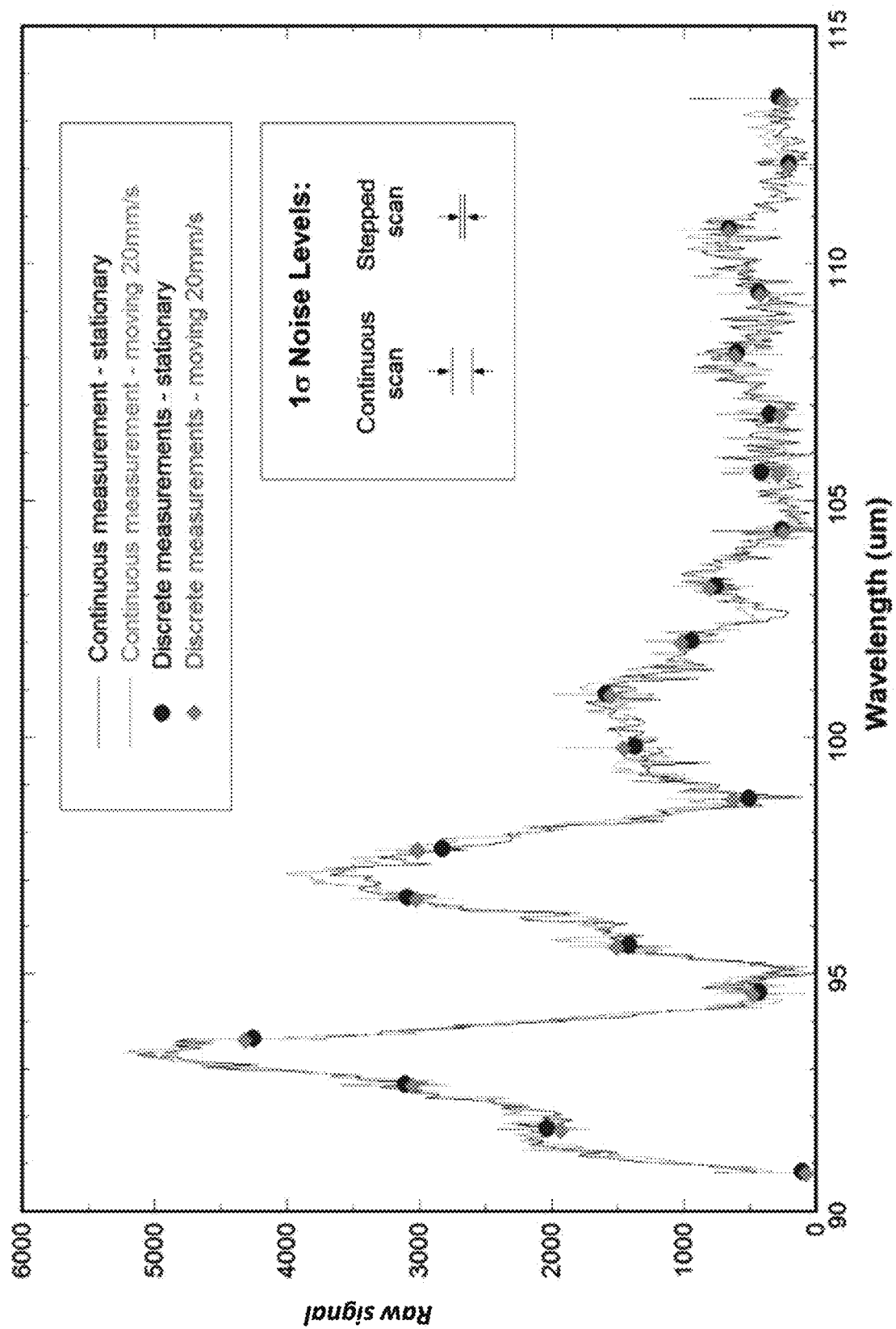
FIG. 3 is a graph demonstrating motion tolerance validation using the glass phantom. k-value encoded signal measurements acquired from the glass phantom (#3 described in Methods) using both the Continuous Scan, and the Targeted and Discrete Set (stepped scan), versions of the MRμT technique. The data are from the specimen i) stationary and ii) moving at 20 mm/s along the analysis direction. The Continuous Scan and the Targeted and Discrete (Stepped Scan) icons illustrate the 1 sigma noise magnitude, with no excitation or encode. The Continuous Scan was acquired with 20 kHz/point bandwidth, and the Targeted and Discrete set with 1 kHz/point bandwidth.
Figure 4A:
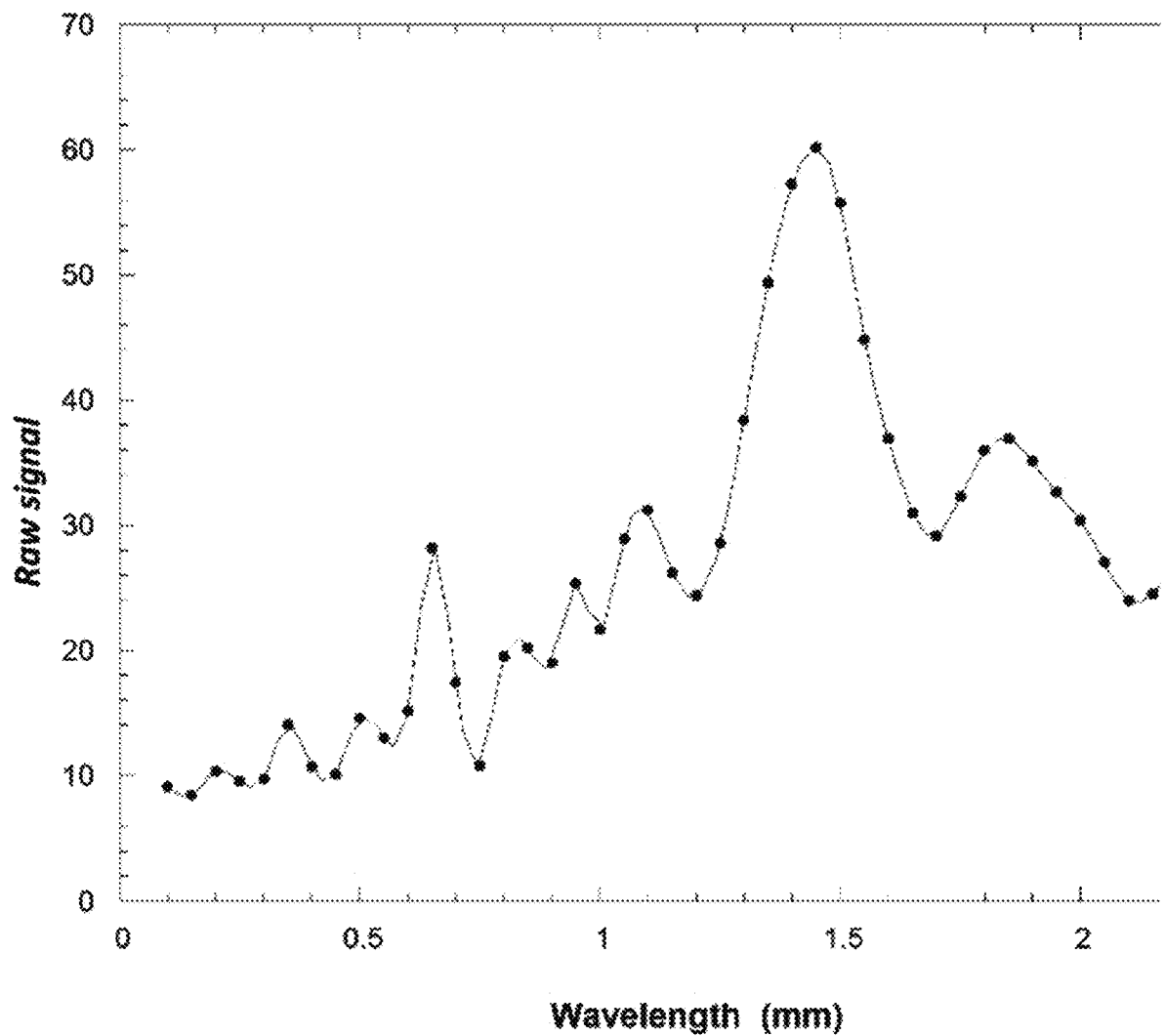
Figure 4B:
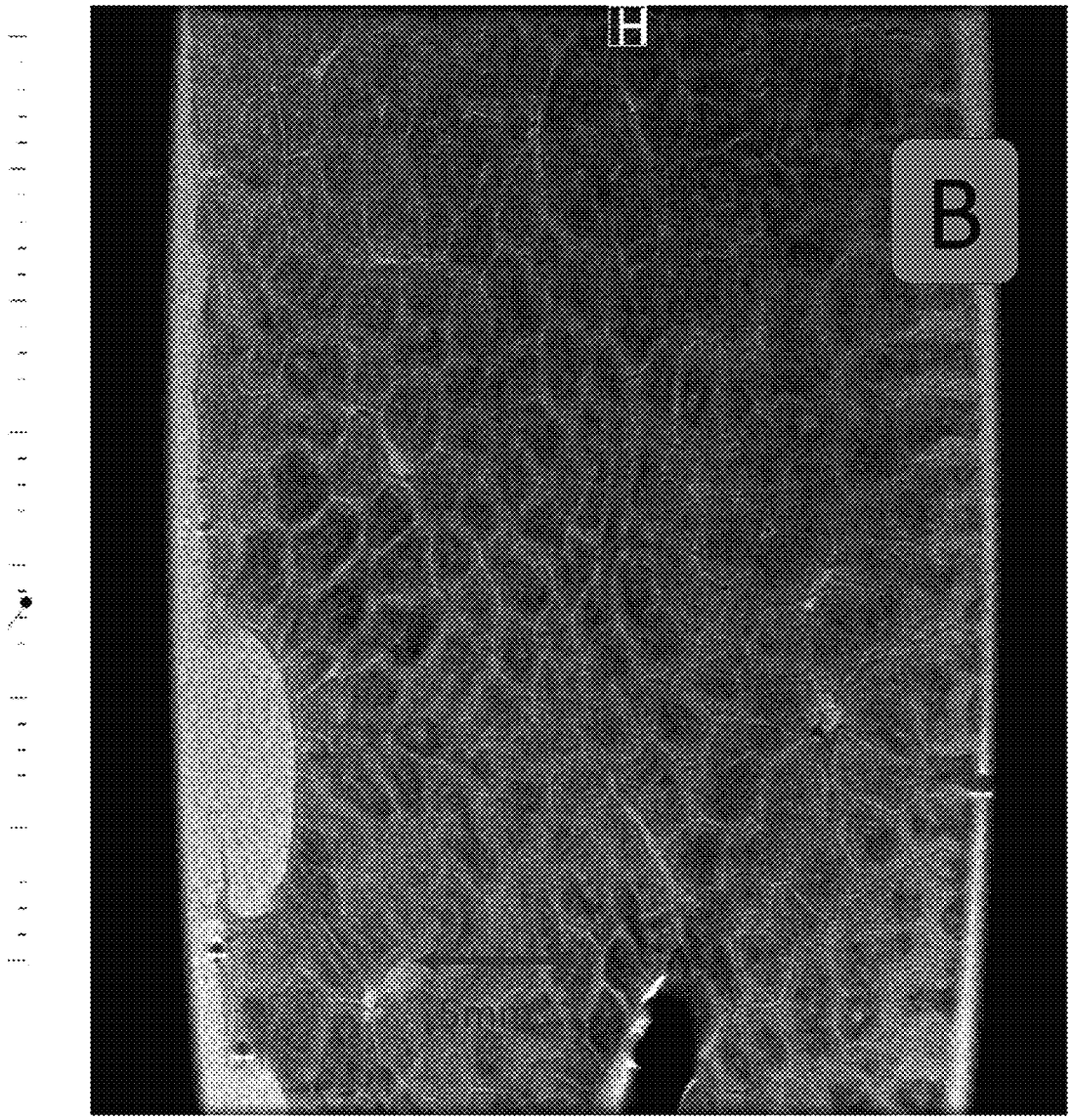

The third implementation of the method, the "Multiple Excitation" method, is shown in FIG. 1C. In this implementation selection of the VOI uses RF excitations 101a-c, slice selection gradients 102a-c, crusher gradients 103a-103d and 103f, and 104a-104f, as described for excitation sequence 100 above. A single k-value (textural wavelength) is encoded with gradient 302 during each excitation sequence. Each excitation in a series of excitations encode a single k-value (spatial wavelength) in the tissue). The gating pulse 306 is applied such that the FID is acquired for the full $T2^*$ period during each TR 106 and an FFT is applied to the data, as will be described subsequently, to yield chemical species information for each specific k-value (textural-wavelength). Integrating or otherwise quantifying the FFT magnitude over the range of the FFT spectrum corresponding to the chemical shift of the species of interest provides a measure for that species at each textural-wavelength (k-encode).

The use of phase cycling offers the opportunity to further enhance SNR and reduce artifacts resulting from the excitation sequence. This technique is applied herein by issuing a series of multiple 180 refocusing pulses after the initial excitation sequence 100 and systematically varying the phases of the exciting and refocusing RF pulses to acquire multiple measurements of the spin echo signal within each TR 106. If originally applied, the k-value selection gradients are reapplied after each refocusing pulse for the selected k-values. The resulting signals with common k-values are then combined to reduce or eliminate certain artifacts, for example coherence path artifacts.

As will be described in greater detail subsequently, the Fourier Transform of the time-resolved data record following each TR or excitation produces an NMR spectrum reflecting the chemical species present at the selected k-encode. (If the k-encode is switched part way through signal acquisition, following an excitation, the data records at each of the k-values can be transformed separately to determine the relative contribution of a chemical species at that point in k-space.) The integrated area under the peaks or other quantification in this NMR spectrum is proportional to the contribution of the chemical species to the textural signal at that k-encode. If there is only one peak in the NMR spectrum then there is only one chemical species capable of producing an NMR signal at the encoded k-value. If there are two or more peaks at a single k-encode, then the texture at that specific k-encode/wavelength contains, in proportion, the various chemical species in the spectrum.

At each new excitation, the VOI can either be positioned as close as possible to where it was in the former excitation, or the VOI can be moved to another part of the tissue or anatomy and data acquired there. To build up a spectrum of textural wavelengths at one location in the tissue, it is not necessary to maintain spatial coherence from one excitation to the next. The only requirement for such characterization is that the VOI remain within a region of similar textural signature. From one excitation to the next, the requirement for VOI positioning is much less stringent than is required in image formation. The requirement that the VOI remain within the region of tissue to be characterized, across multiple acquisitions, can be accomplished by repositioning if the accumulated drift due to motion becomes too large. Again, spatial coherence from one excitation/encode to the next is not required.

Each sequence of excitations may be preceded with a plurality of dummy excitations 304a to equilibrate the sample and followed by a k=0 encoded excitation 304b, for signal level calibration as needed, and a TR with no excitation 304c to gauge system noise.

A multi-point data set (200 points was employed for the measurements herein) without any phase encode or excitation for the measure of system noise.

Data Analysis

In general, data analysis is accomplished with the steps of:
  a. Perform an FFT on the time series data set acquired above thus generating an NMR spectrum of signal intensity vs. PPM chemical shift.
  b. Identify the center frequency of the specimens' NMR spectrum,
  c. Select a span in chemical shift centered on the NMR signal and sum the signal to generate a magnitude measurement (raw signal).

Validation

The high-resolution ability and motion immunity of MRµT was validated using four tailored phantoms and a Bruker 7T preclinical MRI scanner with a maximum gradient capability of 362 mT/m, and 72 mm and 66 mm ID integrated transmit/receive coils. A non-magnetic mechanical driver moving at 20 mm/sec parallel to the bore axis was used to simulate biologic motion.

The four phantom types used for validation of the MRµT method are:
  a. a 3D-printed, 1 mm thick, 4 mm diameter hydrogel disc with a regular hexagonal pattern of channels designed to mimic muscle.(see D. Berry, S. You, J. Warner, L. Frank, S. Chen and S. Ward, "A 3D Tissue-Printing Approach for Validation of Diffusion Tensor Imaging in Skeletal Muscle.," *Tissue Eng Part A.*, vol. 23, no. 17-18, pp. 980-988, 2017). This phantom Error! Reference source not found.A was immersed in phosphate buffered saline for scanning; ground truth for this phantom was provided by optical microscopy. The primary repeating pattern for such a hexagonal array is at a wavelength of 0.866×45 µm center-to-center spacing, hence the dominant textural wavelength is 39 µm.
  b. a glass phantom consisting of a stack of 100 µm thick microscope cover slips spaced apart with 150 µm of water (maintained using plastic shims) mounted in a plastic tube filled with DI water and degassed to avoid bubbles. The third harmonic of the signal was examined. The known dimensions of the stack components and a high-resolution MRI provided ground truth for this phantom.
  c. a 6 mm-diameter bovine femur cancellous bone core with soft tissue removed, immersed in water for scanning.
  d. a fresh pig liver specimen—pig liver was chosen because the delineation of the hepatic lobules by collagen provides a texture in healthy pigs similar to what develops in diseased humans, hence offering a targeted tissue texture in soft tissue that closely resembles an important pathology; a tissue section roughly 20 m×15 m×75 mm was suspended in a plastic tube filled with gelatin to avoid distorting the tissue by compression against the walls of the tube; a combination of optical microscopy, MRI images, and histologic images from the literature, provided ground truth for this third phantom.

As a specific example to relate to an in vivo use of the methods presented herein a Prostate Tissue Specimen was employed.

Prostate Specimen Preparation

Tissue specimens were procured via Stanford and an approved IRB (or in the case of animal tissue, via the food chain). The prostate tissue specimen analyzed in this study was prepared in a similar way to the technique described in R. M. Bourne and et al., "Apparatus for Histological Validation of In Vivo and Ex Vivo Magnetic Resonance Imaging of the Human Prostate.," *Frontiers in oncology*, vol. 7, p. 47, 2017. The results presented herein are from a 4 mm thick by ~30 mm diameter disc-shaped, fixed and paraffin-embedded histology tissue section taken from a central slice of an excised radical prostatectomy tissue sample exhibiting cancerous lesions (Grade 3 with~5% Grade4). The magnetic resonance signal T2 decay time of solid paraffin is too short for imaging; hence, imaging and MRµT data acquisition is from the specimen removed from its microtome cassette and immersed in liquid paraffin at 60C, so that T2 is sufficiently long(see S. Macura, P. K. Mishra, J. D. Gamez and I. Pirko, "MR microscopy of formalin fixed paraffin embedded histology specimens.," *Magnetic resonance in medicine*, vol. 71, no. 6, pp. 1989-1994, 2014). The nominally disc shaped specimen was held between two plastic discs, which were immersed in the liquid paraffin, contained in a 100 ml glass beaker insulated with Styrofoam. This system provided sufficient insulation for ~20 minutes of imaging/data acquisition while the paraffin remained liquid. The image in Error! Reference source not found.B shows a high-resolution MRI image of a 1 mm thick slice through the center of the prostate tissue specimen.

Prostate Tissue Data Acquisition

The Bruker graphical user interface provided positioning guidance to place the analysis VOI in the targeted tissue regions. Multiple VOI were scanned in each of the four regions targeted provided the multiple wavelength samples for characterizing the tissue types.

The Multiple TR method provided multiple wavelength measurements for each targeted VOI—a 50 ms recording of the time domain spin echo signal recorded in quadrature with a dwell time of 250 µs/data point—for 200 data points.

Prostate Tissue Specific Data Analysis

Figure 9:
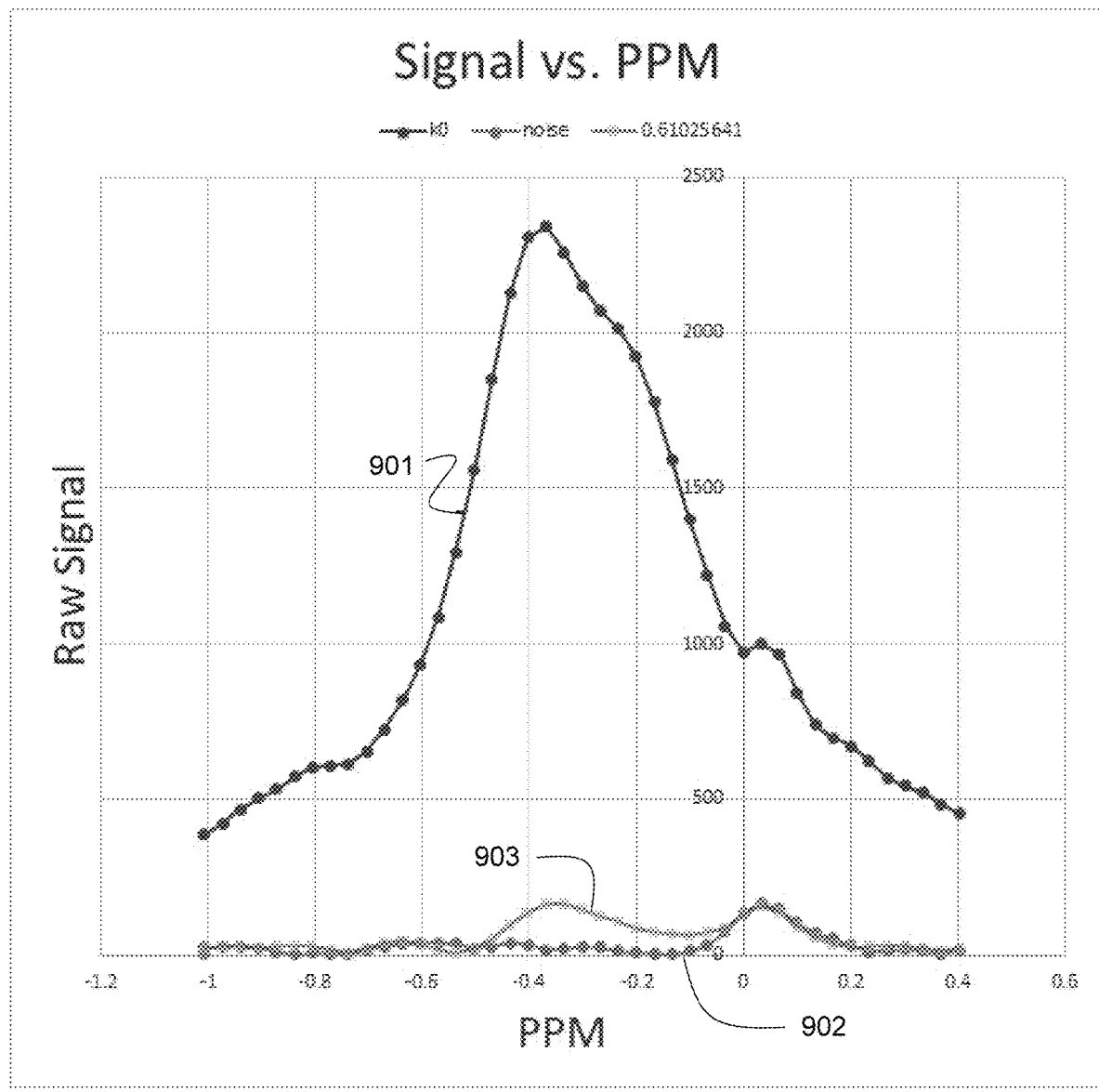
FIG. 9 is a graph of FFT of time series spin echo signal for the case of an excited VOI with no k-encode (k0), with no excitation or encode (noise), and with an encode of 0.61 mm wavelength.

Analysis of each spin echo signal record is as follows:
  a. Perform an FFT on the 200-point time series data set acquired above thus generating an NMR spectrum of signal intensity vs. PPM chemical shift with the system center frequency or other reference frequency defined as 0 PPM as seen in FIG. 9 Wherein trace 901 is the spectrum for k0, trace 902 is the spectrum providing an underlying noise level (i.e. no phase encode and no excitation) and trace 903 is an example spectrum at $\lambda$=0.61025641
  b. Identify the center frequency of the specimens' NMR spectrum 901 from the penultimate TR measurement of the Multiple TR series of excitations ($k_0$ encoded—i.e., no encode) of the targeted VOI by plotting and locating the maximum of the NMR signal vs. chemical shift.
  c. Select a span of ±0.2 PPM in chemical shift (6 data points each way from the peak identified in b) of spectrum 901 above) and sum the signal to generate a magnitude measurement (raw signal) for each wavelength encode and for the ko encoded TR
  d. Select the same span of ±0.2 PPM as in c) above and sum the signal from the ultimate TR spectrum 903 to generate a measure of the noise level (noise).
  e. Calculate a signal for each of the encoded wavelength TR increments using the following formula:

$$\text{signal}(\lambda) = (\text{raw signal}(\lambda) - \text{noise}) / (\text{raw signal}(\infty) - \text{noise})$$

Normalization to the raw signal at $\lambda=\infty$ (i.e., $k_0$ which has no phase encode) provided a means to combine measurements from VOI of different sizes.
  f. Binning of the multiple measurements of signal ($\lambda$) was used as a means to highlight the distribution of feature sizes and is calculated by first segmenting measurements into wavelength bands (bins) and then calculating an average value and range for each wavelength band.

Results

High-Resolution and Motion Immunity

Ability of MRμT to measure fine textures with wavelengths <40 μm: Error! Reference source not found.B shows the measurements made on the hydrogel 3D printed phantom using the Multiple TR MRμT method with a VOI of 2×2×2 mm exhibiting a clear peak at 38 μm (within the precision of our gradient model).

Demonstration of Motion-Tolerance of the MRμT Method:

Error! Reference source not found. presents k-value encoded signal measurements spanning the wavelength range from 91 μm to 113 μm acquired from the glass phantom both stationary and moving at 20 mm/s. The figure is a plot of four data sets (two MRμT methods—with both moving and stationary specimens for each method) acquired using the Continuous Scan and Targeted and Discrete Set MRμT methods as described in Methods. The close coincidence between all the data sets demonstrates that motion does not affect the measured value. The differing sampling time per point does affect the noise level of the measurement as would be anticipated given the longer sampling time per k-encoded measurement in the Targeted and Discrete Set method.

The solid lines in Error! Reference source not found. present the data from the Continuous Scan method acquired with a 20 KHz receiver bandwidth per point. For the Targeted and Discrete Set of measurements, 20 measurements at 20 kHz bandwidth were combined (total sampling time/point=1 ms), thereby reducing the effective receiver bandwidth to 1 kHz and increasing SNR. Strong signals at 93, 97, and 101 μm etc. indicate that these wavelengths are prominent in the sample.

This validation of motion immunity was repeated using a biologic phantom—a bovine femur bone core also exhibiting the coincidence of stationary and moving measurements.

The Ability to Characterize Textures in Biologic Specimens:

Error! Reference source not found. shows the scan data from a pig liver specimen; the data was acquired using the Multiple TR method. Texture wavelength measurements from optical photographs of the tissue specimen prior to mounting in gelatin, and high-resolution preclinical MRI images (Error! Reference source not found.B) obtained after sample mounting, provided ground truth for the texture sizes of the hepatic lobules, the central veins, and the collagen walls. Error! Reference source not found.A shows a typical MRμT spectrum of measurements from this phantom. Textural—wavelength peaks are seen at 0.7, 1.5 and 1.9 mm (obtained by integrating the signal in the water-proton peak of the FFT of the recorded spin echo signal).

Avoidance of Artifacts Resulting From a Finite Analysis Length:

VOI dimensions should be chosen to suit the textural wavelengths of interest in the sample. In particular, the dimension of the VOI in the analysis direction (z) needs to be sufficiently long to avoid artifacts introduced by the slice select profile used to define the length (z) of the VOI. Measurements of a water phantom (which should exhibit no texture signal from the water) indicate that the analysis length of the VOI should be at least 4 times the maximum wavelength of interest to avoid these artifacts. For measured wavelengths <¼ of the VOI length, the effect is minor. All the data presented in this paper adhere to this minimum VOI length.

Prostate Tissue Analysis

Biologic tissues, including prostate, exhibit a multiplicity of textures as compared to the highly ordered synthetic structure in Error! Reference source not found.A. For a proof-of-principle study, MRμT measurements were acquired of the distribution of feature sizes smaller than 1 mm in four regions of the excised prostate gland specimen, exhibiting localized cancers in both the otherwise normal peripheral and transition zones as identified by matching histology. Error! Reference source not found.A shows the optical high-resolution histology image ground truth and a pre-clinical high-resolution 1 mm slice thickness MR image of the corresponding location in the organ. Error! Reference source not found.B also indicates the locations of the four anatomical analysis regions and indicates with a superimposed rectangle 505 the location and lateral extent of one example VOI.

Greater than 900 individual texture wavelength measurements were obtained from 32 VOI distributed across the four regions indicated in Error! Reference source not found.A and 5B. The selection of these representative regions was informed by the guidance of a genitourinary pathologist. These texture measurements consist of raw signal collected at specific k-values (i.e. wavelengths), which were used to construct 32 discrete spectra consisting of 30+ points each.

Figure 5A:
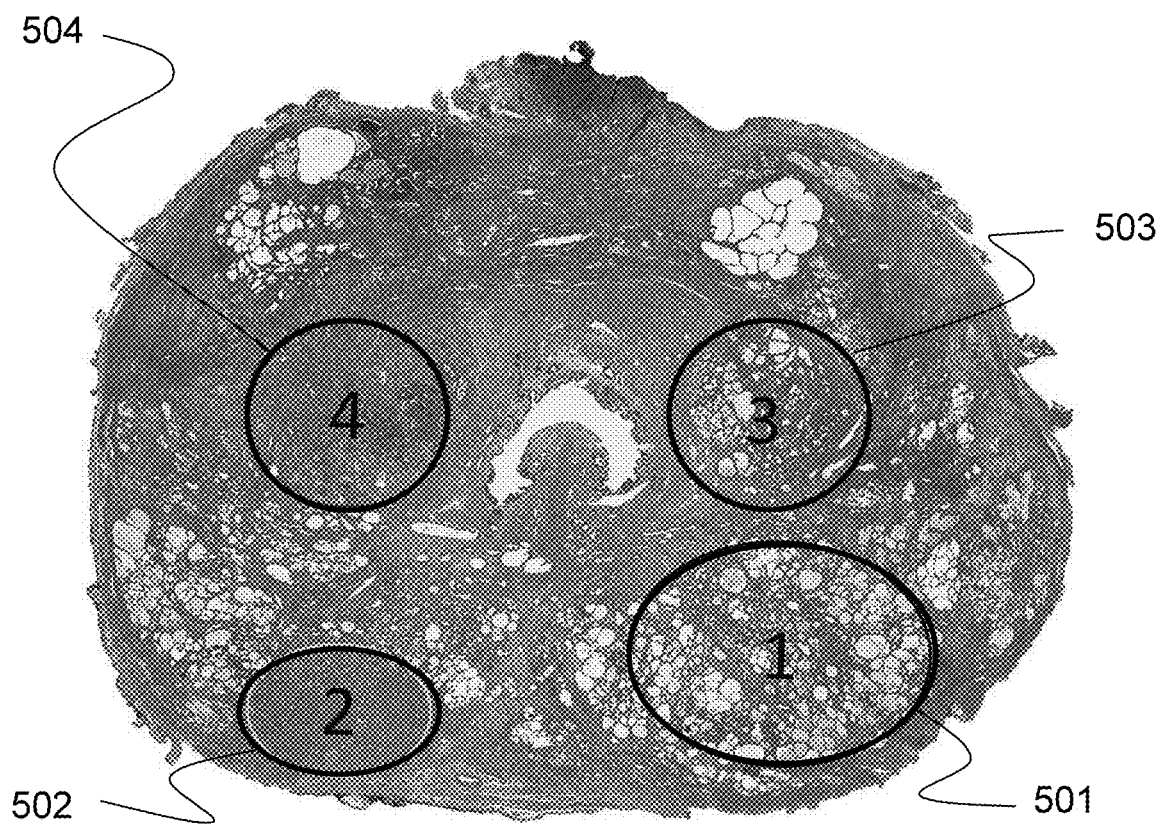
FIGS. 5A and 5B illustrate a prostate specimen analyzed herein with FIG. 5A providing a Histology image and FIG. 5B a corresponding high resolution pre-clinical 1 mm slice MRI image of the 4 mm thick fixed tissue radical prostatectomy specimen analyzed herein. The overlaid rectangle 505 in FIG. 5B indicates one of the VOI locations in the normal tissue of the peripheral zone. Regions 501 and 503 are peripheral and transition zone normal tissue, respectively. Regions 502 and 504 are peripheral and transition zone tumors respectively (mostly Grade 3 with ~5% Grade4).
Figure 5B:
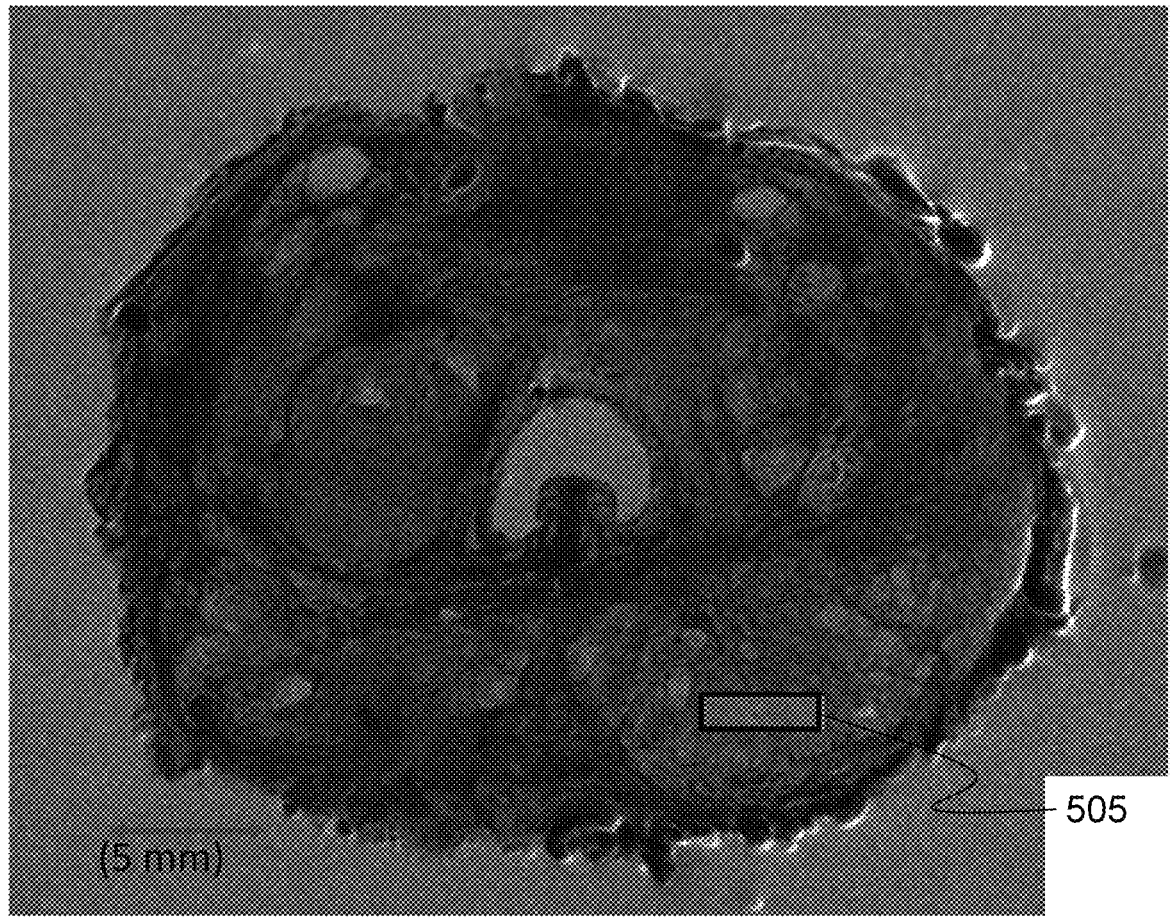
Figure 6:
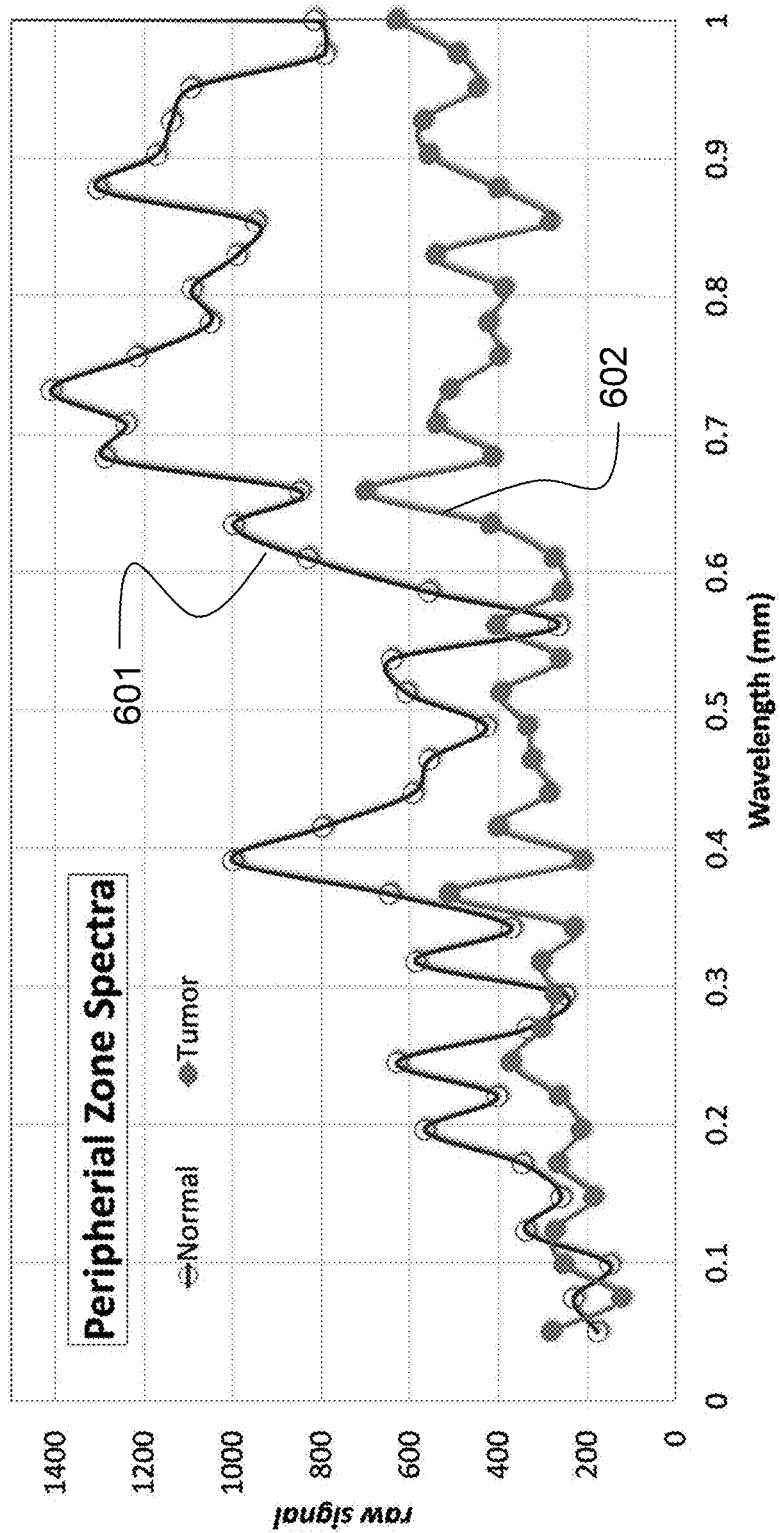
FIG. 6 is a graph of prostate spectra from the normal peripheral (region 501) and tumor peripheral (region 502) regions of the specimen in FIGS. 5A and 5B. Each spectrum is assembled from 39 MRμT point frequency measurements taken using the MRμT Multiple TR method from a 1×1×5 mm VOI within each of the two regions with the k-encode along the 5 mm axis of the VOI. Here the raw signal is plotted with upper curve 602—in the normal peripheral zone of the specimen exhibiting texture groupings at 0.4, 0.7, and 0.9 mm, and lower curve 604—in a tumor in the contralateral region of the peripheral zone (regions 501 and 502 respectively).
Figure 7:
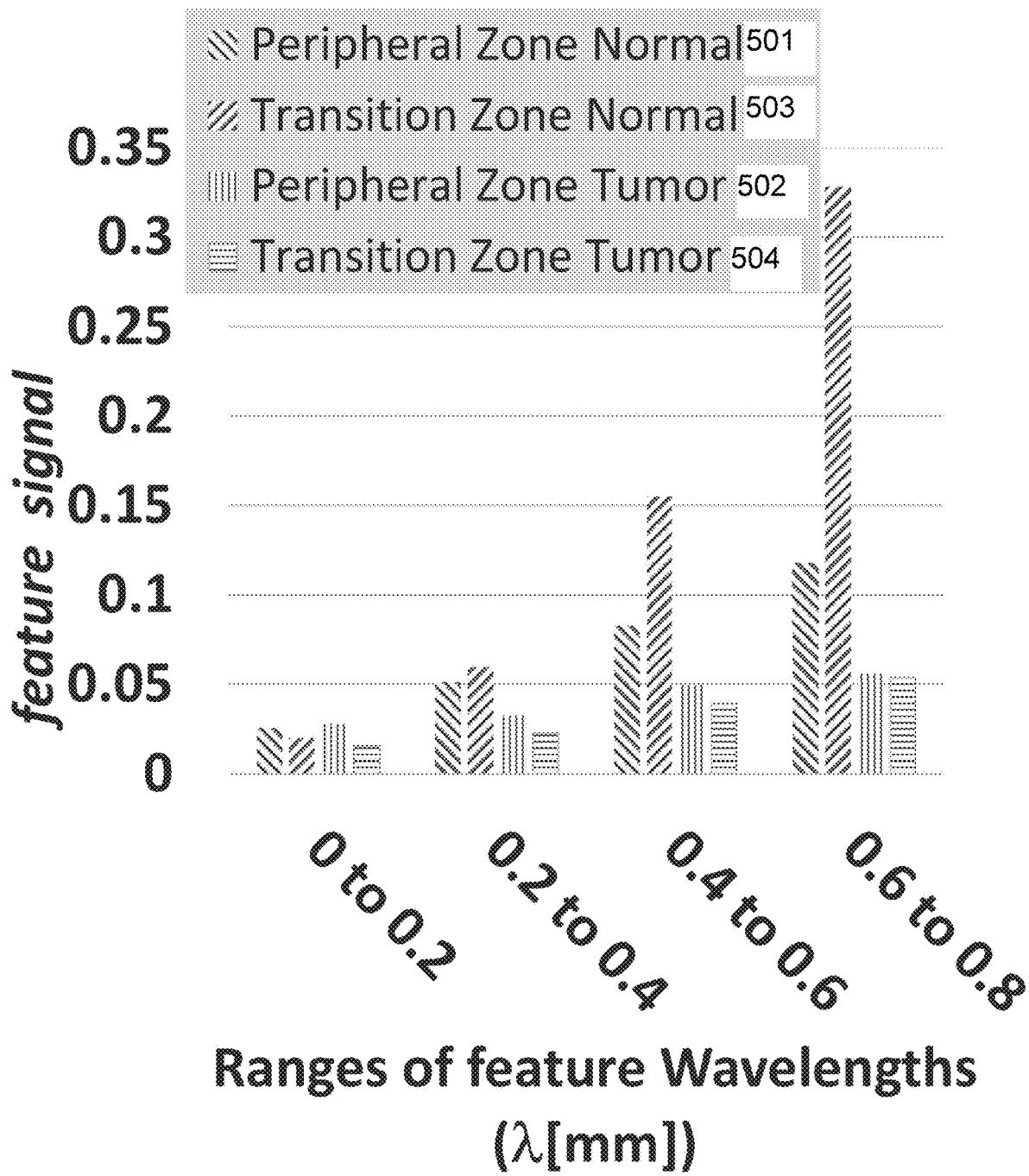
FIG. 7 is a bar graph wherein normal tissue exhibits features at higher wavelengths that are absent in tumor regions. Mean values of the binned feature signal (noise corrected and normalized to k0 +max–min as discussed below in Section 5.2 Prostate Tissue Analysis) for four texture wavelength ranges for the four analyzed regions of the radical prostatectomy specimen of FIGS. 5A and 5B. Note the higher prevalence of coarser textures (i.e., larger structures) represented as feature signal in the normal tissue compared to the tumor tissues.
Figure 8:
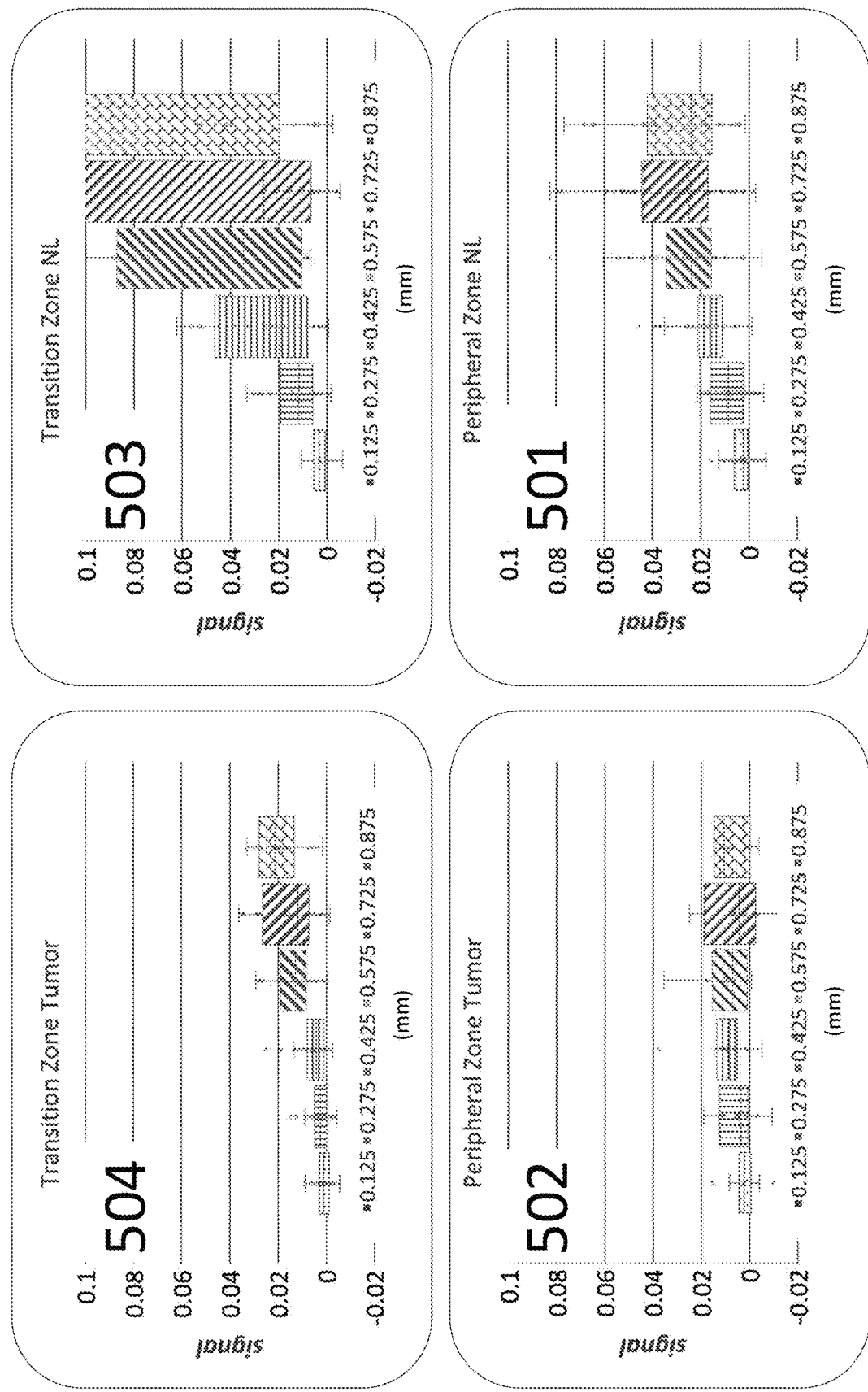
FIG. 8 provides bar graphs of the textural feature statistics (signal [noise corrected and normalized to k0] as described in 4.2.3 d below) extracted from spectral wavelength bins distinguish between normal regions 502 and 504 and tumor regions 501 and 503. Results displayed for six adjacent bins of width 0.15 mm, centered at values ranging from 0.125 mm to 0.875 mm. The results are not sensitive to binning parameters. Feature measurements for mean and variance for normal tissue (regions 501 and 503) increase significantly with wavelength, in sharp contrast to tumor tissue (regions 502 and 504) which have relatively uniform spectra.

Error! Reference source not found. presents two representative spectra with 39 individual texture wavelength measurements each—the spectrum 602 from the cancerous region in the peripheral zone (502 of FIGS. 5A and 5B) and the spectrum 601 from the normal region in the peripheral zone 501 of FIGS. 5A and 5B). Note that the spectrum obtained for the cancerous tissue is more uniform across wavelengths, compared to the normal tissue spectrum. This reflects the relatively uniform texture of the tumor tissue compared to the coarse and variable textures apparent in the normal tissue histology in Error! Reference source not found.A and 5B. Peaks in the normal tissue spectrum reflect the presence of tissue textures that are not present in the cancerous tissue. Qualitatively similar distinctions between relatively uniform spectra in cancerous regions, and variable spectra in normal tissue, are observed across the 32 measured VOI. Specific wavelengths associated with peaks in the spectra vary, reflecting biological variability in the textures.

To quantify distinctions between spectral features in the four regions for the analysis herein, and to combine the 900+ individual measurements, as previously described, noise was subtracted and the signal normalized to the measurement at $k_0$ for each set of measurements within a VOI. For each anatomical region, these MRμT measurements were sorted into four bins, each consisting of a 0.2 mm range of wavelengths. For each bin the feature signal is defined to be the average of the noise-corrected-and-normalized-measurements in the wavelength range of the bin, plus the maximum minus the minimum values within the bin. This extracts the maximum feature size from an individual spectrum in the range defined by the bin. Peaks in the spectra (e.g., Error! Reference source not found.) contribute significantly to the feature signal.

Error! Reference source not found. presents the feature signal from the four anatomical regions of the prostate tissue specimen. The values from normal tissues in regions 501 and 503 increase significantly with feature size (i.e., wavelength) and are larger than the values from the cancerous regions 502 and 504. Less pronounced is the difference in the measured values for cancerous regions 502 and 504 which show a decreasing difference as feature size increases. With respect to the two normal tissue regions—region 503

(Normal transition zone) has a much higher prevalence of structures with larger sizes, i.e. coarser texture, than region 501 (Normal peripheral zone). This can be appreciated by inspection of the histology image and the preclinical MRI image in Error! Reference source not found.A and 5B.

Error! Reference source not found. illustrates corresponding statistical results for six slightly narrower bins than in Error! Reference source not found. with the noise corrected and normalized measurements for each spectrum plotted for six distinct bins of increasing wavelength, thereby reducing each of the 32 spectra (e.g., Error! Reference source not found.) to a six-dimensional feature vector. The feature measurements are sorted by region, and plotted as box plots, where the box ranges from the 25-75 percentile of the measurements within each bin, with outliers displayed individually.

Error! Reference source not found. shows that with increasing wavelength, the normal peripheral and transition zone regions on average show sharp increases in both the average and the variance, consistent with the prevalence of large features and high degree of variability present in normal prostate histology (Error! Reference source not found.A and 5B regions 501 and 503 in both the optical histology image and the preclinical MRI). Increases in the mean and variance in the normal transition zone region with wavelength are significantly higher than in the normal peripheral zone. In contrast, the tumor transition zone and tumor peripheral zone regions are relatively uniform across wavelengths. The transition zone tumor region exhibits a less pronounced but notable rise in the average texture signal with increasing wavelength compared to the peripheral zone tumor region, consistent with Error! Reference source not found. and Error! Reference source not found.

Biomarkers may then be defined as distinguishable variation in feature signal ranges within individual bins over various VOIs or variation in feature signal between bins in the same VOI or combination of both sets of variation.

Discussion

In a demonstration of the extensive structural information available by MR in a motionless subject, As reported in B. L. Edlow and et al., "7 Tesla MRI of the ex vivo human brain at 100 micron resolution.," *Scientific data*, vol. 6, no. 1, p. 244, 2019, 100 µm voxel (200 µm texture wavelength resolution) MRI of an ex-vivo brain, a result that required over 100 hours of scan time and a custom-built receiver array coil. (Note that consistent with the Nyquist criteria—to resolve a texture with a wavelength of 100 µm requires sampling the structure every 50 µm i.e., a 50 µm voxel in an image.)

In contrast, MRµT technology can acquire thousands of individual data points in vivo in less than 1 minute, enabling mapping of microscopic textures across an entire organ. MRµT provides high-resolution, quantitative measures of microscopic tissue textures currently only accessible by biopsy. MRµT output is a highly structured dataset of signal level vs. spatial frequency for each VOI, a format that greatly facilitates application of machine learning techniques to identify patterns in the data, enabling subsequent biomarker identification for gauging disease state. The extracted biomarkers, acquired from an array of VOI, can be mapped across lesions or across an organ to reveal pathologic variability across an organ with the potential to greatly enhance the specificity of MRI in prostate cancer and many other diseases that manifest changes in microscopic tissue texture of organs.

The optimal choice of textural wavelengths targeted for measurement will vary for different diseases and pathologies since the signature tissue texture wavelengths vary. Application to routine clinical diagnosis of specific diseases will require development of an optimally chosen sampling of k-space such that the scan time can be minimized—potentially into the range of seconds. This effort will be informed by the existing histological literature and is anticipated to rely significantly on machine-learning algorithms. Ultimately, this will result in a library of protocols/parameters tailored to specific diseases.

While the technique validation disclosed herein was performed using a 7T preclinical scanner, the pulse sequence parameter space (gradient magnitude and rise times, RF excitation, etc.) is well within the capability and standard range of clinical MRI scanners. Since the technique is implemented entirely in software and is not hardware specific, it can be readily implemented on equipment from different MRI vendors. The technique could easily be appended to a standard MRI protocol, adding only a short time to the overall measurement, while providing valuable information for a more comprehensive diagnosis. Given the technical ease of implementation and the short scan time, there are few hurdles to the widespread implementation of the MRµT technique.

The salient features of the spatial frequency spectra for identifying and differentiating various tissue-texture presentations and their correlation with disease stage would be expected to depend on the anatomy and disease type. In the case of prostate cancer (PCa) it appears that the presence of textures with wavelengths >200 µm is a marker differentiating healthy tissue from cancer. It should be noted that while looking at the data from the perspective of a single measurement from a single patient there is significant overlap between normal and PCa measurements. This illuminates the point that it is the presence of these significant peaks, independent of their precise wavelength that are the distinguishing features.

Conclusions:

This work introduces MRµT a new, motion-immune approach to resolving microscopic tissue textures by magnetic resonance—i.e., histology acquired non-invasively by magnetic resonance. Three implementations of MRµT for soft tissue pathology analysis have been disclosed demonstrating validation of its motion-immune, high-resolution capability providing spatial resolution not achievable by conventional MRI. MRµT is broadly applicable to a wide range of tissue types and diseases, providing non-invasive histology with the potential to displace many invasive biopsies. Example data from human prostate cancer tissue demonstrating the ability to differentiate cancer from normal tissue is presented. MRµT is implemented in software and can be applied to MRI scanners currently in clinical practice, making the translational potential for this method extremely high.

Diagnostic accuracy for the MRµT method relies on accurate determination of the transfer function between the underlying morphologic tissue texture features targeted in a measurement and the diagnostic output data. The term "transfer function" is used in this context to mean the diagnostic calibration that, for a given targeted tissue sample, dictates the output from the MRµT diagnostic. As this is a direct measure of texture, the output textural wavelength spectrum (intensity vs. spatial wavelength) contains all of this information. However, biologic tissues are often relatively complex and varied in morphology. Interpretation of the output data from a diagnostic such as MRµT to yield an accurate measure of the microtexture of the targeted tissue requires careful determination of this transfer function between underlying texture and data output. Determination of the diagnostic calibration/transfer function linking the MRµT data output with tissue texture/pathology state enables sensitive determination of the targeted tissue morphology.

One method to accurately determine this transfer function, or "diagnostic calibration" is through use of high information content /high resolution ground truth data, such as tissue histology. A correlation coefficient is then determined, using a statistically sufficient number of measures, between this ground truth histology measure and the MRµT data from similar tissue.

The highest information content ex vivo ground truth data readily available is 2D histology slice images acquired from the targeted tissue type/disease state and stained to reveal the desired pathologic tissue texture components of interest. This histology can be obtained from postmortem tissue slices, from the literature, or from histology atlases. Additionally, optical microscopy may prove useful in certain tissues to reveal tissue changes to provide ground truth for calibration of the MRµT signal.

For calibration/transfer function determination use of fixed tissue simplifies close correlation between ground truth and MRµT measure by obtaining both the MRµT data and the histopathology from the same tissue block. The MRµT is a 3D measure, while histopathology is 2D, however the histopathology can be obtained from both sides of the MRµT sampled region. Using fixed tissue removes any concern that the tissue block would shrink during histology processing after the MRµT data had been acquired.

Towards clear determination of the transfer function between underlying tissue pathology (reflective of disease stage) and the diagnostic output data, we have developed basic methods that can be applied singly or in conjunction. These rely on in silico modelling of tissue structure and of diagnostic data acquisition. Further, the pattern-recognition capability of AI machine learning analysis techniques can be used to facilitate extraction of diagnostic biomarkers from the data.

Obtaining a 3-dimensional image of the targeted tissue structure noninvasively is fraught due to patient motion causing image blurring, hence reducing image resolution. However, our calibration is accomplished using a combination of very high-resolution ex vivo histology imaging 1) to enable development of very sensitive 2 and 3 dimensional models of these specific tissue structures under study and their pathology changes with disease development, and 2) for accurate understanding of the transfer function that connects the underlying microscopic textures to the diagnostic output.

Developing a highly specific correlation between the output data from the technique and the underlying measured biologic tissue texture in healthy or diseased tissue would be accomplished by using the histology images as the basis of knowledge of a 3D structural representation of a tissue region to be characterized. Then, in silico, the components of this structure would be varied/tweaked in silico and observation made of the resultant change in the in silico acquired MRµT output spectrum. Each microscopic textural/morphologic component can be varied, and the effect on the MRµT spectrum noted.

Magnetic Resonance (MR) imaging in disease diagnosis is rapidly increasing across a broad range of pathologies—it is also a powerful and rich technology with many opportunities remaining for technique improvement. With MRµT a direct method is provided for evaluating pathologic tissue structure down to the tens of µm level. A non-invasive histology diagnostic with this resolution would provide highly desired information that is not available with current diagnostic imaging. This resolution is achieved by focusing on acquisition of only the quantitative microscopic texture data needed for disease assessment rather than on gathering the entire set of data required to generate an image. We present details of this paradigm-changing method, verification of sub-100 µm resolution, and motion immunity. As an example of the many biologic tissue systems that would benefit from quantitative histology measurements non-invasively by MR, MRµT data was acquired from radical prostatectomy tissue with corresponding whole organ optical histology for ground truth. The MRµT data reveal significant differences in tissue texture between cancer and normal prostate tissue indicating the ability to stage disease using this method. Current clinical practice relies on indirect measures and biopsy to diagnose these histologic characteristics which are not resolvable by current imaging modalities including MRI. The MRµT technology is implemented as a new MR pulse sequence. As this is done in software without any requirements for new hardware, it is directly translatable to MRI scanners currently in clinical practice enabling broad adoption to meet the urgent need for improvement in cancer imaging.

In contrast to current clinical imaging, MRµT data acquisition is immune to subject motion by virtue of using a single excitation for each texture measurement. This enables high-resolution, non-invasive measurement of textures in the important sub-100-µm range. This motion immunity is key to avoiding the limitations of traditional clinical MR imaging in which unintentional and involuntary patient movements including respiration, cardiac pulsation, bowel peristalsis, and bladder motion limit resolution. The high-resolution provided by MRµT has the potential to not only identify cancerous lesions, but also to specifically identify aggressive cancers by resolving different cancer grades and potentially avoiding the need for biopsy.

Methods of clinical application of MRµT to prostate cancer (PCa) diagnosis and monitoring are disclosed. The application to PCa is facilitated because of the availability of whole-organ histology (WMHP=Whole Mount Histopathology) and corresponding gland cross-section prostate tissue specimens, which enable one-to-one spatial correspondence of the MRµT measures with high resolution ground truth histology. An additional motivation for this focus on using an MR-based diagnostic is that the utilization of MRI in prostate cancer diagnosis and treatment is rapidly increasing. Scanning is often done using the mpMRI (Multi-Parametric Magnetic Resonance Imaging) scan protocol to acquire data. Recent studies demonstrate the value of current MRI protocols used in tandem with elevated serum prostate specific antigen (PSA) levels for selecting patients for biopsy and in guiding biopsy to improve cancer diagnosis. However, significant unmet challenges remain including more accurate prostate cancer detection on MRI, reducing inter-reader variability of the histology, a need for non-invasive differentiation of indolent vs. aggressive prostate cancer, reduction of long MRI acquisition times, and reducing susceptibility to motion artifact. Biopsy misses PCa in 45% of men—because MRI is widely available, improvements in diagnostic capabilities, particularly ones that can be implemented in software, have the potential to make a major impact in cancer care.

But MRI is not great at distinguishing significant PCa from indolent PCas. Hence, histopathologic examination remains the reference standard today to assign Gleason score to indicate PCa aggressiveness. The wavelength range of interest for PCa is sub 100 µm. Towards evaluation of this shorter wavelength textural components, Diffusion-weighted MRI (DWI) is used, and has become a standard component of mpMRI as it is sensitive to tissue microstructure changes in PCa. A particular embodiment of DWI, Diffusion-Relaxation Correlation Spectrum Imaging (DR-CSI) is used in an attempt to determine the combination of cellular -level morphology that is most likely to result in the observed data from the gland.

Fixed tissue has been used to calibrate the MRµT diagnostic for application to PCa diagnosis and staging. Data was acquired by MRµT from various regions across the ex vivo prostate gland that exhibited varying tissue microtexture pathophysiology, and the acquired data then correlated with the histology acquired from the same regions. As the MRµT data is highly structured, it can be readily input to a machine learning algorithm to identify patterns in the data that correlate with the histology reads. This biomarker extraction method enables high accuracy calibration of the diagnostic. As a result, it is possible to draw a correlation between the MRµT spectrum and the underlying soft tissue texture pathology in prostate tissue. This same type of calibration is possible in other soft tissue such as liver tissue, for staging liver disease. This determination is best made in tissue samples and then by using whatever diagnostic biomarkers were extracted for training the data, towards understanding in vivo data obtained clinically.

Prostate Parameter Space:

By ensuring tissue contrast is sufficient, MRµT can provide a direct, noninvasive diagnostic measure of microscopic tissue texture in the size scale between tens of microns and the much larger scale measurable by clinical imaging. This size range is vital to diagnosing a wide range of diseases.

As was determined by studies of the windowing function and its effect on the acquired data, VOI length must be at least a minimum of 4 texture wavelengths. Due to high textural wavelength variability in some tissues, it is probably better to sample at least 6-8 wavelengths.

One of the diagnostic markers for staging PCa appears to be the presence or absence of longer wavelength features in the micro textural wavelength spectra from particular regions.

Though this is an apparent marker, it is best to measure the variability in micro-textural wavelength across a selected range of the spectrum, rather than just looking at the average over a bin of that selected wavelength range. There is additional diagnostic information in the variance across the spectrum, more than the biomarker obtained from the smoothed wavelength variation across the spectrum. Just like anisotropy, wavelength variability would be expected to contain information on disease stage. This is seen in PCa in the fact that it appears to be the presence of a particular wavelength but rather presence/absence of longer wavelengths.

MRµT resolves the tissue textures by a combination of 1) measuring a targeted set of k-values to characterize texture—as in diffraction analysis of materials—2) performing a selective internal excitation to isolate a VOI, 3) applying a high k-value phase encode to the excited spins in the VOI, and 4) acquiring each individual k-value data point (or band of k-values) in a single excitation—providing motion immunity and extended acquisition time for maximizing SNR. Additional k-value measurements from the same region can be made to characterize the tissue texture in that region— there is no need for these additional measurements to be spatially coherent as there is no image to be reconstructed. This method can be applied to tissue specimens or in vivo clinical scanning toward building up a library of MRµT data signal vs. pathology read. By ensuring tissue contrast is sufficient, MRµT can provide a direct, noninvasive diagnostic measure of microscopic tissue texture in the size scale between tens of microns and the much larger scale measurable by clinical imaging. This size range is vital to diagnosing a wide range of diseases.

The data reveal textural differences not resolvable by standard MR imaging. As MRµT is a pulse sequence, it is directly translatable to MRI scanners currently in clinical practice to meet the need for further improvement in cancer imaging. Depending on the tissue you are measuring, you can get an idea of the distribution of textural wavelength that will need to be recorded using a literature search of applicable histology.

To obtain a measure of noise and to normalize the data to the measurement at k0 (use k) as intensity reference:

a. Position the VOI in multiple orientations/positions for data acquisition and acquire MRµT data b. For each anatomical region, these MRµT measurements were sorted into four bins, each consisting of a 0.2 mm range of wavelengths. For each bin the feature signal is defined to be the average of the noise corrected and normalized measurements in the wavelength range of the bin, plus the maximum, minus the minimum values. This extracts the maximum feature size from an individual spectrum in the range defined by the bin. Peaks in the spectra (e.g., Error! Reference source not found.) contribute significantly to the feature signal.

c. Build up a library of feature signals or direct MRµT output and apply machine AI algorithms (machine learning/deep learning) for pattern recognition I the data and to enable extraction of biomarkers from the data for correlation with ground truth histology reads. These reads can be from MRµT acquired from either prostate tissue samples, or from in vivo clinical measure. These biomarkers are used to calibrate the MRµT diagnostic by correlation with Gleason score/tumor aggressiveness histology reads towards use in clinical diagnosis.

d. Compare between data measurement and library

Error! Reference source not found. shows that, with increasing wavelength, the normal peripheral and transition zone regions on average show sharp increases in both the average wavelength spectrum intensity and the variance in the spectrum intensity. This is consistent with the prevalence of large features and high degree of variability visible in normal prostate histology (Error! Reference source not found.A and 5B regions 501 and 503 in both the optical histology image and the preclinical MRI). Increases in the mean spectrum intensity and the spectral variance in the normal transition zone region with wavelength are significantly higher than in the peripheral zone. In contrast, the tumor transition zone and tumor peripheral zone regions are relatively uniform across wavelengths. The transition zone tumor region exhibits a less pronounced but notable rise in the average texture signal with increasing wavelength compared to the peripheral zone tumor region, consistent with Error! Reference source not found. & Error! Reference source not found. To gather this data, it is possible to perform multiple excitations—i.e. to use multiple TRs.)

Additional points on calibration of the MRµT diagnostic for application in prostate, and other soft tissue, diseases:

For application of MRµT to prostate disease (and other soft tissue diseases such as liver and kidney) an accurate calibration of the diagnostic is needed—i.e. accurate understanding of the transfer function between underlying tissue texture/pathology and the MRµT output signal. This calibration can be developed in part through use of in silico analysis.

Possible inputs to this analysis are:
a. Histology images from both ends of the ground truth prostate (or other tissue) tissue slabs used for diagnostic calibration
b. Pathologist read of these end slice histology images
c. The MRµT output data from the tissue slab Using these 3 data sources it is possible, using machine/deep learning techniques to develop an accurate calibration of MRµT as a diagnostic.

Pattern recognition is developed between the multiplicity of ground truth and MRµT data from each tissue sample, using multiple VOIs to cover the entire cross-sectional prostate gland tissue slabs.

A correlation is developed between the ground truth histology and the MRµT data.

The histology is a 2D measure whereas MRµT is a 3D acquisition—using the two end-slab histology images, it is possible to develop a multiplicity of 3D interpolations of the tissue between these two end-slices. There are multiple possible morphologies to connect the two end images. Varying the intermediate tissue steps used in the model, can yield information on the sensitivity of the diagnostic to the exact structure in the prostate tissue slab.

Using in silico modeling, the structure of the tissue texture in the slab can be tweaked as a function of position across the slab to yield a structural unfolding through the thickness of the tissue sample slab. MRµT data can be acquired in silico as a function of tissue model across the slab, providing MRµT output as a function of this modeled structure, and the effect of this tissue texture variation on diagnostic output tracked. The second stage is correlation between a pathologist's read of the images, with the MRµT output for training the diagnostic calibration/transfer function.

When the correlation between the modeled tissue texture and the MRµT data is well-developed, this correlation can be expanded to correlating the MRµT data and the pathologists read—i.e. supervised development of the transfer function between MRµT data output and disease, to enable disease staging.

Other tissue pathologies for which MR is increasing used for diagnosis and staging is in liver disease/liver cancer, as well as for diagnosis and staging of other forms of cancer. For instance, in staging soft tissue cancers, moving the VOI across a lesion/hyperintensity that is apparent in MR imaging, to obtain an MRµT spectrum vs. position and orientation would enable delineation of tumor perimeters, as the microvessel and tissue structure is known to change in the region of a tumor.

Combining MRµT with Data Acquisition Methods Similar to Asl (Arterial Spin Labeling) and DWI (Diffusion Weighted Imaging)

Many diseases can be diagnosed and tracked based on microvessel pathology development in the affected organ. An important example of the need for assessing vessel pathology is in COVID-19—research indicates that the neurologic damage that often manifests with the disease appears to be caused not by presence of the virus in the affected region, but as a result of pathology such as blood clotting and inflammation driven by viral infection in elsewhere in the anatomy. In many cases of brain pathology arising from COVID-19 no signs of SARS CoV-2 are found in tissue samples, indicating that the observed brain damage is not caused by direct viral attack but by microvascular blood vessel damage elsewhere, with attendant symptoms such as vessel thinning and leakage. Leaky vessels resulting in breaching of the blood brain barrier is a noted symptom in various forms of dementia, again implicating vessel damage as a causative pathology.

Healthy tissue perfusion is necessary to ensure nutrient distribution and removal of metabolic byproducts, and for body temperature regulation. Compromised blood vasculature underlies much disease response. However, a high-resolution diagnostic is required to probe the state of the micro-vasculature—a method to make microvessel pathology manifest is needed.

ASL (Arterial Spin Labeling) offers an MR-based measure of tissue perfusion and assessment of vascular pathology. There are clear benefits to the technique, the main one being that it is a completely non-invasive measure, relying as it does on endogenous MR contrast, and hence is ideal for pediatric populations, patients with renal insufficiency, and those needing repeat follow-ups. However, though ASL can measure perfusion in tissue, it does not enable the resolution necessary to measure the textural morphology of the microvessels driving the perfusion.

The basic ASL method uses the ability of MR scanners to magnetically label, or "tag", the arterial blood water protons in a slice upstream of the imaging slab. This can be achieved by various methods that result in different signal intensities in the various tissues. But this ability to magnetically label tissue, enables a differential measurement of the static MR image before and after the tagged bolus reaches the image plane. The initial image is identical to the magnetically tagged slice, except for the signal from the tagged blood flowing into the slab used for data acquisition, hence differential analysis of the two images highlights the aggregate micro-vasculature. The most commonly derived property obtained using this method is cerebral blood flow (CBF).

ASL cannot provide the high-resolution measure of the micro-vasculature needed to sensitively and accurately diagnose and track neuropathology, due to intrinsic limitations. A major difficulty is the low SNR of ASL—the signal from the blood water protons is only about 0.5% to 1.5% of the full tissue signal. Further, because ASL relies on the replacement of untagged by tagged blood, reasonably high arterial velocities are required to obtain good differentiation between the two images. But flow rate is limited by stenoses and other pathologic blockages. Further, limited temporal resolution—a main source of errors is arterial transit time—combined with the low SNR, makes for low (Contrast to Noise Ratio) CNR for the technique. Additionally, the measured image is subject to blurring by patient motion in between acquisition of the untagged vs. tagged signals—any motion between the two acquisitions smears the perfusion measure. Also, the ASL acquisition takes approximately 10 minutes, rather long when added to the rest of an imaging protocol.

For these various reasons ASL has not developed as a standard measure of perfusion in the brain. What ASL can do is to provide a reasonable measure of the blood flow rate into various organ tissue, providing an image that can, on a macro scale, highlight regions exhibiting vessel pathology.

There is, however, currently no method to accurately and sensitively assess early-stage brain histopathology arising from micro-vessel degradation—imaging is limited by patient motion blurring, and biopsy is not an option in the brain. PET scanning is invasive (relying on radionuclides) and expensive, not an option for repeat measure for pathology tracking. Though ASL is designed to provide macro-scale imaging of vessel response across the brain, it is not able to provide the high-resolution measure needed to accurately assess micro-vessel pathology development in neuropathology. However, these measurements can be made by magnetically tagging blood water to generate contrast for the MRµT measurement.

The loss of image resolution in ASL arising from patient motion in between each tagged and untagged image acquisition can be solved by acquiring both the tagged and the untagged signal within one excitation. This would not be possible for imaging but becomes possible by combining blood water tagging upstream of the tissue for which micro-vasculature needs assessing with the MRµT data acquisition method. As described in our body of issued and filed patents, the MRµT acquisition is not an image acquisition but rather acquisition of a targeted set of k-values pertinent to the targeted pathology. Each k-value in the desired set is acquired within a single excitation making it motion immune. And acquisition of a small set of k values in a single excitation greatly increases SNR because the limited data set required for MRµT enables acquisition of multiple repeats of one or a few k-values. The motion immunity of MRµT and its high SNR, when combined with magnetic tagging of blood water, can enable non-invasive, high resolution measure of micro-vasculature.

A few methods for combining blood tagging with the paradigm changing data acquisition method of MRµT are:

Magnetic tagging of a bolus of blood upstream of the tissue region where we want to position the VOI to acquire MRµT data from microvessels. As with ASL, the magnetic tagging is used to provide contrast between the blood flow and the stationary tissue background intensity, highlighting the micro-vasculature. The MRµT ability for averaging of multiple repeats of each targeted k-value provides significantly higher SNR to the measurement than would be available with ASL.

A further step to add contrast between the blood and the background tissue intensity is to first kill the tissue signal from the background (no tagged blood) tissue, in advance of the magnetically tagged bolus moving into the targeted VOI. Using the MRµT acquisition method to acquire tissue texture data from the slab with killed tissue signal and tagged blood provides a very high CNR measure of the micro-vasculature within the VOI, wherever placed within the region of tagged blood.

If a differential measure, similar to that used in ASL, is desired, MRµT has the ability to get past the resolution loss resulting from patient motion between measure of the background and of the tagged tissue images that occur when in this acquisition mode. Not only is the data acquisition method of MRµT (single excitation k-value recording) immune to patient motion during signal recording, but the loss of resolution arising from patient motion during the delay between acquisition of the untagged and tagged data can be circumvented. This is accomplished by acquiring the untagged and tagged flow within the same excitation by MRµT, acquiring data at a single, or at a band of k-values continuously as the labeled blood flows into the VOI. Refocusing the signal will extend the available recording time, allowing increased signal averaging and higher SNR. The differential measure can be achieved by exciting the blood bolus upstream of the VOI and tracking the output/VOI MRµT measure temporally—excite blood and then watch it flow in to yield a continuous differential measure.

Further highlighting of the tagged micro-vasculature signal against background can be obtained by chemical identification of the blood in the vessels via determination of the phase shift of the MRµT signal from the vasculature, a method outlined in a previous patent.

Application of machine learning/deep learning to the data acquired in any of the methods described above is facilitated by the fact that the data output is highly structured. The details of the application of these techniques will differ depending on the specific data output.

For instance, if the endogenous blood contrast (magnetically tagged blood bolus) is used simply as a contrast agent in each measurement, machine learning can be used to find patterns in the dataset of repeat VOI acquisitions, using these as an unsupervised measure, to study the variation across the set of repeats from each targeted k-value measure. Pattern recognition across these sets will provide a measure of the variability of the data—how "stable" it is across multiple measures. Further, any available tissue ground truth, such as histology, can then be used for supervision of the blood flow data.

For the experiments for which a differential measure of tagged and untagged tissue is recorded, the same pattern recognition can be applied to this differential measure, again applying ground truth supervision as possible. This also provides a different dataset in that the multiple refocuses enable signal intensity vs. time measures, to yield an assessment of rate of blood flow through the micro-vasculature.

The combination of MRµT and magnetic tagging offers the ability to non-invasively, and accurately and sensitively, assess the micro vessel pathophysiology underlying many neurologic disorders and conditions. This combination enables the ability to non-invasively provide diagnostic information on the resolution scale of biopsy-driven histology. This is a paradigm change in ability to diagnose these conditions, enabling earlier diagnosis, input to therapy design, and tracking of therapy response.

Another technique, Diffusion Weighted Imaging (DWI), uses the effect of pathology-driven changes in cellular morphology on water diffusion to diagnose and track disease. DWI is used for diagnosis in many different pathologies including stroke triage, detecting and staging tumors, whole body imaging, various cancers and diseases throughout the anatomy.

The basic method of DWI that measures cellular textures by use of the changes they engender in water diffusion can be combined with MRµT method of acquisition to enable direct measure of tissue microtextures.

MRµT can measure textural features down to tens of microns; DWI is looking at micro-structural features on the order of a few microns. This means that the combination of these two techniques covers the cellular up through microstructural range enabling textural evaluation across an extremely important range of tissue texture sizes for disease diagnosis and staging. The two techniques could be used as separate measurements. It is also possible to use the defocusing and refocusing DWI measure of ADC (Apparent Diffusion Coefficient) as contrast for data acquisition in multi-repeat acquisitions of targeted k-values within single excitations.

Setting parameters for these measurements and developing data analysis methods can be facilitated through use of in silico modelling of tissue and of data acquisition. The aim is to maximize SNR and CNR, and data analysis towards 1) optimizing the information content of the MRµT measurement output and 2) calibrating the diagnostic to enable predicting the output signal expected from various textural features that are markers of disease. The transfer function between the underlying tissue texture/morphology and the MRµT output signal is needed here.

For techniques involving diffusion weighting, this is relatively complex as DWI is an indirect technique—the measured signal can arise from a plurality of underlying tissue morphologies. Further, the flow dynamics affecting signal development from a magnetically labeled bolus of blood traversing a specific micro-vessel morphology is affected by stenoses and other vessel pathology. Nonetheless, simulation of the MRμT data acquisition using DWI to measure tissue texture, or using magnetically labeled blood for contrast, is able to be done. Use of a series of morphologic and chemical models of micro-texture and micro vessel structures can be used to demonstrate how the output signals correlate with the underlying textural morphology. Hence, the textural input models can be tweaked and the resulting changes in the data output observed. Developing these models facilitates calibration of the combined diagnostics—i.e. determination of the transfer function between the MRμT data output and the underlying tissue texture, including micro-vasculature.

STATEMENTS OF INVENTION

Application of the MRμT method, for prostate disease diagnosis, staging, and monitoring, as well as determination of pathophysiology towards therapy determination, using the MRμTexture diagnostic measurement to differentiate normal from cancerous prostate tissue in prostate disease and identify the specific tissue micro-textures associated with varying Gleason score.

Using the MRμT method to measure prostate tissue textural morphology in the approximately 500 μm down to tens of μm spatial wavelength size scale range to help determine the tissue pathophysiology of the various stages of prostate disease Application of machine learning/deep learning algorithms to obtained MRμT data to develop pattern recognition in the MRμT output data, using high resolution histologic ground truth to supervise the data for extraction of disease biomarkers and disease grading.

Deriving quantities from the MRμT tissue feature measurement data and correlating these features in the MRμT output data with high resolution ground truth, such as tissue pathophysiologic histology MR-microscopy, or optical microscopy to define biomarkers of disease stage in prostate disease, enabling non-invasive differentiation of indolent vs. aggressive prostate cancer.

Using the MRμTexture matrix/spectrum of signal intensity vs. spatial wavelength output by the MRμTexture diagnostic of tissue texture to grade prostate disease.

Using the MRμT data of signal intensity vs. spatial wavelength output by the MRμT method of tissue texture to determine pathophysiology and etiology towards designing therapeutics Use of in vivo MRμT data to calibrate this method for in vivo clinical use by acquiring data across the prostate and correlating it with biopsy driven pathology reads for grading prostate disease.

Using the fact that normal prostate tissue presents with a higher prevalence, and variability, of long wavelength features in comparison with tumor tissue which has a relatively flat variation in intensity with increasing wavelength to distinguish normal from cancerous tissue.

Use of prostate tissue samples—either fixed or fresh—in conjunction with high resolution ground truth such as pathology, MR-microscopy and/or optical microscopy to build up libraries of prostate histology vs. MRμT data output, using pattern recognition in conjunction with supervised data interpretation through histology reads to extract biomarkers for grade of prostate disease/Gleason score.

Use of variable binning parameters for analyzing the MRμT data towards determination of optimal biomarkers of disease onset and progression, correlating the binned data with histology reads.

Obtaining MRμT data from prostate tissue by embedding the tissue in paraffin just above melting temperature to increase MR contrast hence resulting in higher contrast to noise data for training the diagnostic.

The biomarkers derived from binning of texture wavelength data and ratioing or other combining of the various textural wavelength regions.

Use of measurement of the spatial distribution of feature sizes smaller than 1 mm in different regions throughout excised prostate gland specimens exhibiting both cancerous and normal tissue in both the peripheral and transition zones, as identified by matching histology, and using these features and their distribution as identifiers to diagnose and stage PCa.

Data processing by subtracting a noise measurement (output signal with no input) and normalizing to k0, for each set of measurements within a VOI.

Sorting the output noise-corrected and normalized signal vs. wavelength data into wavelength bins for each prostate region, each consisting of a sub 1 mm range of wavelengths. For each bin the feature signal is defined to be the average of the noise corrected and normalized measurements in the wavelength range of the bin, plus the maximum, minus the minimum values. This extracts the maximum feature size from an individual spectrum in the range defined by the bin.

Using MRμT to provide noninvasive histology in place of (highly invasive) biopsy when added to mpMRI prostate disease diagnostic scans.

Using the thousands of individual data points acquired in vivo to mapping the defined biomarkers across an organ using the identified biomarkers for disease diagnosis and tracking.

Mapping of the extracted biomarkers across lesions or across organs to reveal pathologic variability across an organ with the potential to greatly enhance the specificity of MR-based information in prostate cancer and many other diseases that manifest changes in microscopic tissue texture of organs.

Use of measurement of tissue textures with wavelengths >200 μm as a marker differentiating healthy tissue from cancerous tissue in the prostate.

Measurement of the tissue textures from prostate tissue from different anatomical regions for prostate staging whereby feature distribution with wavelength and across legions/regions can be used to stage prostate disease/determine Gleason score.

Use of the intensity profile versus wavelength—both average and standard deviation, and all derivatives thereof, as potential markers for disease stage.

Development of a library of protocols/parameters tailored to specific diseases

Use of MRμT measurements in conjunction with use of magnetic blood tagging/labeling for contrast, to determine the texture/morphology of micro-vessels in the body.

Use of MRμT measurements in conjunction with magnetic blood tagging/labeling to determine the temporal filling of vascular structures as a function of vessel network texture.

Use of differential measurement to highlight vascular textures between pre- and post-blood flow bolus arrival in our data-recording plane.

Use of histology-informed computer modeling of tissue textures, to assist in the development of an accurate transfer function between tissue texture/pathology and the MRµT output.

Tweaking these modeled textures and tracking the MRµT output data changes resulting from each specific modeled texture change.

Use of the correlation between the in silico modeled tissue texture data and the MRµT data output for determination of the transfer function/calibration of the MRµT diagnostic.

What is claimed is:

1. A method for measuring soft tissue texture to identify diseased as opposed to normal tissue, the method comprising:
   identifying textural markers in a ground truth that distinguish diseased tissue from normal tissue;
   selecting a MRµT excitation sequence comprising a Multiple TR series and associated parameters to reveal said markers;
   acquiring data in an MR scanner responsive to the selected MRµT excitation sequence to establish a multipoint time series data set by performing a selective internal excitation of a Volume of Interest (VOI) within a targeted tissue region;
   imposing a spatial-frequency phase encode for a targeted tissue textural-wavelength, $\lambda$ (or k-value), of interest along a texture analysis direction within the VOI; and
   recording a resulting signal; and
   analyzing the acquired data for presence of said markers by
      performing a FFT on the multipoint time series data set acquired to generate an NMR spectrum of signal intensity vs. PPM chemical shift with a system center frequency as 0 PPM;
      identifying a center frequency of the NMR spectrum from a selected TR measurement of the Multiple TR series of excitations of the targeted VOI by plotting and locating the maximum of the NMR signal vs. chemical shift;
      selecting a span in chemical shift and summing the signal over the span to generate a magnitude measurement as a raw signal for each wavelength encode and for the k0 encoded TR;
      selecting the span and summing the signal from an ultimate TR to generate a measure of noise level (noise);
      calculating the signal for each of the encoded wavelength TR increments as
         signal($\lambda$)=(raw signal($\lambda$)-noise)/(raw signal($\infty$)-noise); and
      binning the multiple measurements of the signal to highlight distribution of feature sizes.

2. The method as defined in claim 1 wherein binning comprising segmenting measurements into wavelength bands defining a plurality of bins and then calculating an average value and range for each wavelength band in the VOI.

3. The method as defined in claim 1 further comprising:
   identifying distinctions between first spectra indicating the markers between cancerous regions and second spectra indicating normal tissue based on the ground truth; and,
   designating feature signal ranges corresponding to the identified distinctions as biomarkers for disease identification.

4. The method as defined in claim 3 wherein identifying distinctions comprises
   determining a prevalence of large features and high degree of variability in texture in contrast to relatively uniform texture across wavelength bins.

5. The method as defined in claim 1 wherein identifying textural markers in a ground truth that distinguish diseased tissue from normal tissue comprises creating data input by one or more of:
   extracting texture data from histology images of ground truth tissue slabs used for diagnostic calibration;
   inputting pathologist read data of histology images; or
   comparing MRµT output data from a tissue slab.

6. The method as defined in claim 5 further comprising using machine learning to create pattern recognition of the texture markers.

7. A method for obtaining soft tissue texture to identify biomarkers for diseased as opposed to normal tissue in a prostate, the method comprising:
   acquiring data of a signal using a Multiple TR method with a targeted VOI for
      a multi-point time series data set for range of wavelengths each with a single k-value (textural wavelength) encoded during each excitation (TR), wherein subsequent TRs encode different k-values, with spin echo recorded for a full T2* period;
      a normalizing dataset in a penultimate TR at $k_0$; and
      a multi-point dataset with no encode or excitation in an ultimate TR to generate a measure of noise;
   performing a FFT on the multi-point time series data set acquired including k0 to generate an NMR spectrum of signal intensity vs. PPM chemical shift with the system center frequency as 0 PPM;
   identifying a center frequency of the NMR spectrum from a penultimate TR measurement of the Multiple TR series of excitations of the targeted VOI by plotting and locating the maximum of the NMR signal vs. chemical shift-;
   selecting a span in chemical shift and summing the signal to generate a magnitude measurement as a raw signal for each wavelength encode and for the TR encoded at $k_0$;
   selecting the span of and summing the signal from the ultimate TR with no excitation as the noise level (noise);
   calculating the signal for each of the encoded wavelength TR increments as
      signal($\lambda$)-(raw signal($\lambda$)-noise)/(raw signal($\infty$)-noise);
   binning the multiple measurements of the signal by segmenting measurements into wavelength bands (bins) and then calculating an average value and range for each wavelength band;
   identifying distinctions based on markers defined in a ground truth between uniform spectra indicating cancerous regions and variable spectra indicating normal tissue; and,
   designating feature signal ranges corresponding to the identified distinctions as biomarkers for disease identification.

8. The method as defined in claim 7 wherein the span is ±0.2 PPM.

9. The method as defined in claim 7 wherein the ground truth comprises a histology image and a corresponding MRI image of a 4 mm thick by ~30 mm diameter disc-shaped section, fixed and paraffin-embedded histology tissue section taken from a central slice of an excised radical prostatectomy tissue sample of an ex vivo prostate gland exhibiting cancerous lesions and MRµT data acquired using the Multiple TR method from various regions across the ex vivo prostate gland that exhibited varying tissue micro-texture pathophysiology, and the acquired data then correlated with the histology acquired from the same regions.

* * * * *